(12) United States Patent
Woodell-May et al.

(10) Patent No.: US 10,946,043 B2
(45) Date of Patent: Mar. 16, 2021

(54) METHODS OF MEDIATING MACROPHAGE PHENOTYPES

(71) Applicant: Biomet Biologies, LLC, Warsaw, IN (US)

(72) Inventors: Jennifer E. Woodell-May, Warsaw, IN (US); Joel C. Higgins, Claypool, IN (US); William King, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 255 days.

(21) Appl. No.: 15/797,796

(22) Filed: Oct. 30, 2017

(65) Prior Publication Data

US 2018/0050063 A1 Feb. 22, 2018

Related U.S. Application Data

(62) Division of application No. 14/554,381, filed on Nov. 26, 2014, now Pat. No. 9,833,474.

(60) Provisional application No. 61/928,284, filed on Jan. 16, 2014, provisional application No. 61/909,249, filed on Nov. 26, 2013.

(51) Int. Cl.
*A61K 35/15* (2015.01)
*C12N 5/0775* (2010.01)
*C12N 5/0786* (2010.01)
*A61K 35/16* (2015.01)

(52) U.S. Cl.
CPC ............ *A61K 35/15* (2013.01); *C12N 5/0645* (2013.01); *C12N 5/0667* (2013.01); *A61K 35/16* (2013.01); *C12N 2501/20* (2013.01); *C12N 2502/1382* (2013.01)

(58) Field of Classification Search
CPC ...... A61K 35/15; A61K 35/16; C12N 5/0645; C12N 2501/20
See application file for complete search history.

(56) References Cited

U.S. PATENT DOCUMENTS

| | | |
|---|---|---|
| 4,708,799 A | 11/1987 | Gerlach et al. |
| 4,853,137 A | 8/1989 | Ersson |
| 5,075,222 A | 12/1991 | Hannum et al. |
| 5,359,032 A | 10/1994 | Dayer et al. |
| 5,571,418 A | 11/1996 | Lee et al. |
| 5,585,007 A | 12/1996 | Antanavich et al. |
| 5,599,558 A | 2/1997 | Gordinier et al. |
| 5,707,331 A | 1/1998 | Wells et al. |
| 5,788,662 A | 8/1998 | Antanavich et al. |
| 5,792,450 A | 8/1998 | Wilson et al. |
| 5,842,477 A | 12/1998 | Naughton et al. |
| 6,063,297 A | 5/2000 | Antanavich et al. |
| 6,096,728 A | 8/2000 | Collins et al. |
| 6,214,338 B1 | 4/2001 | Antanavich et al. |
| 6,287,558 B1 | 9/2001 | Lanza et al. |
| 6,337,072 B1 | 1/2002 | Ford et al. |
| 6,398,972 B1 | 6/2002 | Blasetti et al. |
| 6,599,873 B1 | 7/2003 | Sommer et al. |
| 6,623,472 B1 | 9/2003 | Reincke et al. |
| 6,649,072 B2 | 11/2003 | Brandt et al. |
| 6,713,246 B1 | 3/2004 | Reinecke et al. |
| 6,759,188 B2 | 7/2004 | Reinecke et al. |
| 6,790,371 B2 | 9/2004 | Dolecek |
| 6,811,777 B2 | 11/2004 | Mishra |
| 6,835,377 B2 | 12/2004 | Goldberg et al. |
| 6,905,612 B2 | 6/2005 | Dorian et al. |
| 7,011,852 B2 | 3/2006 | Sukavaneshvar et al. |
| 7,166,283 B2 | 1/2007 | Tsuji et al. |
| 7,179,391 B2 | 2/2007 | Leach et al. |
| 7,223,346 B2 | 5/2007 | Dorian et al. |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,867,765 B2 | 1/2011 | Faustman et al. |
| 7,901,344 B2 | 3/2011 | Yoo |
| 7,901,584 B2 | 3/2011 | Dorian et al. |

(Continued)

FOREIGN PATENT DOCUMENTS

| | | |
|---|---|---|
| AU | 748575 B2 | 6/2002 |
| EP | 0417818 A1 | 3/1991 |

(Continued)

OTHER PUBLICATIONS

Cao et al., IL-10/TGF-beta-modified macrophages induce regulatory T cells and protect against adriamycin nephrosis. Journal of the American Society of Nephrology, vol. 21, No. 6 (Jun. 2010) pp. 933-942. (Year: 2010).*
Antonios et al., Macrophage polarization in response to wear particles in vitro. Cellular & Molecular Immunology, vol. 10 (online Sep. 9, 2013) pp. 471-482. (Year: 2013).*
"European Application Serial No. 14812109.8, Communication Pursuant to Article 94(3) EPC dated Oct. 20, 2017", 4 pgs.
"European Application Serial No. 14812109.8, Reference filed Oct. 16, 2017 to Office Action dated Mar. 27, 2017", 12pgs.
"U.S. Appl. No. 14/554,381, Final Office Action dated Mar. 3, 2017", 11 pgs.
"U.S. Appl. No. 14/554,381, Non Final Office Action dated Sep. 8, 2016", 8 pgs.

(Continued)

*Primary Examiner* — Kara D Johnson
(74) *Attorney, Agent, or Firm* — Schwegman Lundberg & Woessner, P.A.

(57) ABSTRACT

Methods of inducing a polarization of macrophages. The method includes obtaining a blood fraction, fractionating the blood fraction to produce a blood fraction, and contacting the blood fraction with a source of macrophages. A blood fraction including platelet-poor plasma polarizes the source of macrophages into M1 macrophages. A blood faction including a protein solution polarizes the source of macrophages into M2 macrophages.

20 Claims, 6 Drawing Sheets

(56) References Cited

U.S. PATENT DOCUMENTS

| | | |
|---|---|---|
| 7,914,689 B2 | 3/2011 | Higgins et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,202,539 B2 | 6/2012 | Behnam et al. |
| 8,753,690 B2 | 6/2014 | Higgins et al. |
| 9,833,474 B2 | 12/2017 | Woodell-May et al. |
| 2001/0053764 A1 | 12/2001 | Sims et al. |
| 2002/0077276 A1 | 6/2002 | Fredeking et al. |
| 2002/0119179 A1 | 8/2002 | Rezania et al. |
| 2003/0055511 A1 | 3/2003 | Schryver et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0194397 A1 | 10/2003 | Mishra |
| 2003/0205538 A1 | 11/2003 | Dorian et al. |
| 2004/0120942 A1 | 6/2004 | Mcginnis et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0084962 A1 | 4/2005 | Simon |
| 2005/0100536 A1 | 5/2005 | Mishra |
| 2005/0109716 A1 | 5/2005 | Leach et al. |
| 2005/0152905 A1 | 7/2005 | Omoigui |
| 2005/0186120 A1 | 8/2005 | Dorian et al. |
| 2005/0196874 A1 | 9/2005 | Dorian et al. |
| 2005/0197293 A1 | 9/2005 | Mellis et al. |
| 2006/0046960 A1 | 3/2006 | Mckay et al. |
| 2006/0051865 A1 | 3/2006 | Higgins et al. |
| 2006/0057223 A1 | 3/2006 | Dimauro et al. |
| 2006/0057693 A1 | 3/2006 | Simon |
| 2006/0121002 A1 | 6/2006 | Rolland et al. |
| 2006/0171948 A1 | 8/2006 | Weinstein et al. |
| 2006/0175244 A1 | 8/2006 | Dorian et al. |
| 2006/0175268 A1 | 8/2006 | Dorian et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0075016 A1 | 4/2007 | Leach |
| 2007/0092494 A1 | 4/2007 | Higgins et al. |
| 2007/0207161 A1 | 9/2007 | Ralph |
| 2008/0011684 A1 | 1/2008 | Dorian et al. |
| 2008/0019964 A1 | 1/2008 | Olmarker et al. |
| 2008/0064626 A1 | 3/2008 | Zanella |
| 2008/0193424 A1 | 8/2008 | Mckale et al. |
| 2008/0217263 A1 | 9/2008 | Higgins et al. |
| 2008/0268064 A1 | 10/2008 | Woodell-may |
| 2008/0269762 A1 | 10/2008 | Simon et al. |
| 2008/0306431 A1 | 12/2008 | Yoo |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | De Wildt et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0198130 A1 | 8/2010 | Swift et al. |
| 2010/0226909 A1 | 9/2010 | Hecker et al. |
| 2010/0256595 A1 | 10/2010 | Leach et al. |
| 2011/0052561 A1 | 3/2011 | Hoeppner |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0129441 A1 | 6/2011 | Lentz |
| 2011/0189172 A1 | 8/2011 | Solinger et al. |
| 2011/0192804 A1 | 8/2011 | Landrigan et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |
| 2012/0150086 A1 | 6/2012 | Cohen |
| 2012/0172836 A1 | 7/2012 | Higgins et al. |
| 2013/0178425 A1 | 7/2013 | Higgins et al. |
| 2013/0259951 A1 | 10/2013 | O'Connell |
| 2014/0242045 A1 | 8/2014 | Higgins et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |
| 2014/0271870 A1 | 9/2014 | O'Shaughnessey et al. |
| 2014/0274893 A1 | 9/2014 | Woodell-May et al. |
| 2014/0274894 A1 | 9/2014 | Leach et al. |
| 2014/0274895 A1 | 9/2014 | Binder et al. |
| 2014/0275497 A1 | 9/2014 | Leach et al. |
| 2015/0141332 A1 | 5/2015 | Toler |
| 2015/0147300 A1 | 5/2015 | Woodell-May et al. |

FOREIGN PATENT DOCUMENTS

| | | |
|---|---|---|
| EP | 2186877 A2 | 5/2010 |
| EP | 2639313 A1 | 9/2013 |
| WO | WO-9108285 A1 | 6/1991 |
| WO | WO-9905989 A2 | 2/1999 |
| WO | WO-9967277 A1 | 12/1999 |
| WO | WO-03063799 A2 | 8/2003 |
| WO | WO-03080104 A2 | 10/2003 |
| WO | WO-03088905 A2 | 10/2003 |
| WO | WO-2004009207 A1 | 1/2004 |
| WO | WO-2006043972 A1 | 4/2006 |
| WO | WO-2007121538 A1 | 11/2007 |
| WO | WO-2007128973 A2 | 11/2007 |
| WO | WO-2008021237 A1 | 2/2008 |
| WO | WO-2011031553 A2 | 3/2011 |
| WO | WO-2012030593 A2 | 3/2012 |
| WO | WO-2012040310 A2 | 3/2012 |
| WO | WO-2013102193 A1 | 7/2013 |
| WO | WO-2015081253 A1 | 6/2015 |

OTHER PUBLICATIONS

"U.S. Appl. No. 14/554,381, Notice of Allowance dated Aug. 24, 2017", 7 pgs.

"U.S. Appl. No. 14/554,381, Response filed Jun. 1, 2017 to Final Office Action dated Mar. 3, 2017", 14 pgs.

"U.S. Appl. No. 14/554,381, Response filed Aug. 19, 2016 to Restriction Requirement dated Jun. 21, 2016", 7 pgs.

"U.S. Appl. No. 14/554,381, Response filed Dec. 5, 2016 to Non Final Office Action dated Sep. 8, 2016", 11 pgs.

"U.S. Appl. No. 14/554,381, Restriction Requirement dated Jun. 21, 2016", 7 pgs.

"Arthritis", [Online]. Retrieved from the Internet: Wayback Machine <URL:http://www.mayoclinic.org/diseases-conditions/arthritis/basics/treatment/con-20034095 >, (2014), 5 pgs.

"Bio-Rad Laboratories. Bio-Gel P Polyacrylamide Gel Instruction Manual", [Online]. Retrieved from the Internet: <www.bio-rad.com/webmaster/pdfs/9154 Bio-Gel P.pdf>, (Jun. 20, 2012), 14 pgs.

"European Application Serial No. 14812109.8, Office Action dated Mar. 27, 2017", 5 pgs.

"European Application Serial No. 14812109.8, Office Action dated Jul. 13, 2016", 1 pg.

"European Application Serial No. 14812109.8, Response filed Jan. 20, 2017 to Office Action dated Jul. 13, 2016", 9 pgs.

"GPS® II Platelet Concentrate System: The New Gold Standard", Product Brochure, (Sep. 2006), 14 pgs.

"GPS® II System, Gravitational Platelet Separation System", User Manual-Cell Factor Technologies, Inc., [Online]. Retrieved from the Internet: <http://www.cellfactortech.com/global_products.cfm,>, (Sep. 16, 2005), 13 pgs.

(56) References Cited

OTHER PUBLICATIONS

"GPS® II System, Gravitational Platelet Separation System, Accelerating the Body's Natural Healing Process", Cell Factor Technologies, Inc., [Online] retrieved form the internet: <http://www.cellfactortech.com/global_products.cfm>, printed Sep. 16, 2005, (2005), 16 pgs.
"GPS® III Platelet Separation System, Leadership through Technology", Biomet Biologics, Inc, (Jul. 2007), 8 pgs.
"GPS® Platelet Concentrate System", Cell Factor Technologies, Inc Biomet Orthopaedics, Inc., (Feb. 29, 2004), 9 pgs.
"International Application Serial No. PCT/US2014/067702, International Preliminary Report on Patentability dated Jun. 9, 2016", 13 pgs.
"International Application Serial No. PCT/US2014/067702, International Search Report dated Mar. 27, 2015", 8 pgs.
"International Application Serial No. PCT/US2014/067702, Written Opinion dated Mar. 27, 2015", 11 pgs.
"Isolation of Granulocytes From Human Peripheral Blood by Density Gradient Centrifugation", Miltenyi Biotec GmbH, (2008), 2 pgs.
"Plasmax Plasma Concentrate", Biomet Biologics, Inc, Brochure, (2006), 6 pgs.
"Plasmax® Plasma Concentration System", Biomet Biologics, (Mar. 2007), 18 pgs.
"Shoulder Recovery with the GPS® Platelet Concentrate System, Rotator Cuff Surgical Techniques", Biomet Biologics, Inc., (2004), 6 pgs.
"Update for veterinarians", Anonymous, [Online]. Retrieved from the Internet: <URL:http://vet.osu.edu/sites/default/files/documents/pdf /news/vmc/ovmaVeterinarianUp/documents/pdf/news/vmc/ovmaVeterinarianUp>, (Dec. 2012).
"Vortech Concentration System Product", Biomet Biologics, Inc., (Aug. 2005), 16 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andia, Isabel, et al., "Platelet-rich plasma for managing pain and inflammation in osteoarthritis", Nature Reviews Rheumatology, vol. 9. No. 12., (Oct. 1, 2013), 721-730.
Anitua, Eduardo, et al., "Autologous platelets as a source of proteins for healing and tissue regeneration", Thromb Haemost, vol. 91, (2004), 4-15.
Arend, W, et al., "Interleukin-1 Receptor Antagonist: Role in Biology", Annu. Rev. Immunol., vol. 16, (1998), 27-55.
Baltzer, A W, et al., "Autologous conditioned serum (Orthokine) is an effective treatment for knee osteoarthritis. Osteoarthritis Cartilage", (Feb. 1, 2009), 152-60.
Becker, C, et al., "Efficacy of epidural perineural injections with autologous conditioned serum for lumbar radicular compression an Investigator-initiated, prospective, double-blind, reference-controlled study", (2007), 1803-1808.
Bendele, Alison M, et al., "Combination Benefit of Treatment With the Cytoki Ne Inhibitors interleukin-1 Receptor Antagonist and Pegylated Soluble Tumor Necrosis Factor Receptor Type I in animal models of Rheumatoid Arthritis", Arthritis & Rheumatism, Wiley, US, vol. 43, No. 1, (Dec. 1, 2000), 2648-2659.
Bielecki, T, et al., "Antibacterial effect of autologous platelet gel enriched with growth factors and toher acive substances", J Bone Joint Surg, vol. 89-B, No. 3, (Mar. 2007), 417-420.
Burnouf, T, "Blood-derived, tissue engineering biomaterials", Biomedical Engineering-Applications, Basis & Communications, val. 16, No. 6, (Dec. 6, 2004), 294-304.
Couper, Kevin N, et al., "Parasite-Derived Plasma Microparticles Contribute Significantly to Malaria Infection-Induced Inflammation through Potent Macrophage Stimulation", Plos Pathogens vol. 6. No. 1., (Jan. 29, 2010).
Dallari, et al., "Enhanced Tibial Osteotomy Healing with Use of Bone Grafts Supplemented with Platelet Gel or Platelet Gel and Bone Marrow Stromal Cells", The Journal of Bone and Joint Surgery, vol. 89, (2007), 2413-2420.
Dinarello, C, "Interleukin-1 and Interleukin-1 Antagonism", Blood, vol. 77, No. 8, (Apr. 1991), 1627-1652.
Dinarello, C A, "Interleukin-1 in the pathogenesis and treatment of inflammatory diseases", Blood, 2011, vol. 117(14) (2011), 3720-3732.
Eppley, et al., "Platelet Quantification and Growth Factor Analysis from Platelet-Rich Plasma: Implications for Wound Healing", Plastic and Reconstructive Surgery, 114(6), (Nov. 2004), 1502-1508.
Evans, C H, "Novel biological approaches to the intra-articular treatment of osteoarthritis", BioDrugs, (2005), 355-62.
Feige, U, et al., "Anti-interleukin-1 and anti-tumor necrosis factor-alpha synergistically inhibit adjuvant arthritis in Lewis rats", Cmls Cellular and Molecular Li Fe Sciences, Bi Rkhauser Verlag, Heidelberg, DE, vol. 57, No. 10, (Sep. 1, 2000), 1457-1470.
Fiotti, et al., "Atherosclerosis and Inftammation. Patterns of Cytokine Regulation in Patients with Peripheral Arterial Disease", Atherosclerosis. Elsevier Ireland Ltd. IE, vol. 145, No. 1, (Jul. 1, 1999), 51-60.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Hou, W H, et al., "Microftuidic Devices for Blood Fractionation", Micromachines, (2011), 319-343.
Juge-Aubry, C, et al., "Adipose Tissue is a Major Source of Interleukin-1 Receptor Antagonist: Upregulation in Obesity and Inflammation", Diabetes, vol. 52, (May 2004), 1104-1110.
Kaufman, A, et al., "Human macrophage response to UHMWPE, TiAIV, Coer, and alumina particles: Analysis of multiple cytokines using protein arrays", Journal of Biomedical Materials Research Part A, published online in Wiley InterScience, (Jul. 2007), 464-474.
Kim, Seon Hee, et al., "Ex vivo gene delivery of Il-1 Ra and soluble TNF receptor confers a distal synergistic therapeutic effect in antigen-induced arthritis", Molecular Therapy, vol. 6, No. 5, (Nov. 1, 2002), 591-600.
Kimble, Robert B, et al., "Simultaneous block of interleukin-1 and tumor necrosis factor is required to completely prevent bone loss in the early postovariectomy period", Endocrinology, The Endocrine Society, US, vol. 136, No. 7—Abstract, (Jul. 1, 1995), 1 pg.
King, William, et al., "A Simple Method to Correlate the Concentration of an Anti-Inflammatory Cytokine with White Blood Cells in an Autologous Protein Solution", [Online]. Retrieved from the Internet: <URL:http://prgmobileapps.com/AppUpdates/ors/Abstracts/abs391.html>, (Feb. 24, 2014).
Kitazawa, R, et al., "Interleukin-1 Receptor Antagonist and Tumor Necrosis Factor Binding Protein Decrease Osteoclast Formation and Bone Resorption in Ovariectomized Mice", Journal of Clinical Investigation, American Society for Clinical Investigation, US, vol. 94, No. 6, (Dec. 1, 1994), 2397-2406.
Klingenberg, et al., "Treating inflammation in Atherosclerotic Cardiovascular Disease: Emerging Therapies", European Heart Journal., vol. 30, No. 23, (Dec. 2009), 2838-2844.
Lavi, Galia, et al., "Sustained delivery of IL-1 Ra from biodegradable microspheres reduces the number of murine 816 melanoma lung metastases", Journal of Controlled Release, 123, (2007), 123-130.
Lucarelli, E, et al., "Platelet-derived growth factors enhance proliferation of human stromal stem cells", Biomaterials, vol. 24, (2003), 3095-3100.
Mantovani, A, et al., "Macrophage polarization: tumor-associated macrophages as a paradigm for polarized M2 mononuclear phagocytes", Trends in Immunology, Elsevier Ltd vol. 23. No. 11, (Sep. 19, 2002), 549-555.
Mantovani, A, et al., "The chemokine system in diverse forms of macrophage activation and polarization", Trends in Immunology, Elsevier Ltd, Trends Journals, GB, vol. 25, No. 12, (Dec. 1, 2004), 677-686.
Matthews, J, et al., "Comparison of the response of primary human peripheral blood mononuclear phagocytes from different donors to

(56) References Cited

OTHER PUBLICATIONS challenge with model polyethylene particles of known size and dose", Biomaterials, vol. 21, (2000), 2033-2044.

Meijer, H, et al., "The production of antiinflammatory cytokines in whole blood by physico-chemical induction", Inftamm. Res. vol. 52, (Oct. 2003), 404-407.

Mia, S, et al., "An optimized Protocol for Human M2 Macrophages using M-CSF and IL-4/IL-10/TGF- [beta] Yields a Dominant Immunosuppressive Phenotype", Scandinavian Journal of Immunology vol. 79. No. 5, (Apr. 20, 2014), 305-314.

Morizaki, et al., "The Effects of Platelet-Rich Plasma on Bone Marrow Stromal Cell Transplants for Tendon Healing in Vitro", J. Hand Surg. Am., vol. 35, No. 11, (Nov. 2010), 1833-1841.

Murphy, Michael P, et al., "Autologous Bone Marrow Mononuclear Cell Therapy Is Safe and Promotes Amputation-Free Survival in Patients With Critical Limb Ischemia", Journal of Vascular Surgery, C.V. Mosby Co., St. Louis, MO, US, vol . 53, No. 6, (Jan. 28, 2011), 1565-1574.

Muzio, M, et al., "Interleukin-13 Induces the Production of Interleukin-1 Receptor Antagonist (IL-1ra) and the Expression of the mRNA for the Intracellular (Keratinocyte) Form of IL-1ra in Human Myelomonocylic Cells", Blood, vol. 83, No. 7, (Apr. 1994), 1738-1743.

Nursen, Duzgun, et al., "Cytokine inhibitors: soluble tumor necrosis factor receptor 1 and interleukin-1 receptor antagonist in Behcet's disease", Rheumatology International ; Clinical and Experimental Investigations, Springer, Berlin, DEvol. 25, No. 1,, (Jan. 2005), 1-5.

Okunishi, K, et al., "Hepatocyte Growth Factor Significantly Suppresses Collagen-Induced Arthritis in Mice", The Journal of Immunology, vol. 179, No. 8, (Oct. 15, 2007), 15 pgs.

O'Shaughnessey, Krista M, et al., "Blood-derived anti-inflammatory protein solution blocks the effect of IL-1 beta on human macrophages in vitro", Imflammation Research, vol. 60, No. 10,, (Oct. 1, 2011), 929-936.

Rader, C, et al., "Cytokine Response of Human Macrophage-like Cells After Contact With Polyethylene and Pure Titanium Particles", The Journal of Arthroplasty, vol. 14, No. 7, (Oct. 1999), 840-848.

Scull, Christopher M, et al., "Macrophage pro-inflammatory cytokine secretion is enhanced following interaction with autologous platelets", Journal of Inflammation, Biomed Central, London, GB, vol. 7, No. 1, (Nov. 11, 2010), 53 pgs.

Shounan, Vi, et al., "IFN-gamma but not IL-4 is important for mouse CD4+ T cell-mediated macrophage activation following their exposure to pig cells in vitro", Xenotransplantation, vol. 9. No. 4, (Jul. 1, 2002), 268-276.

Simutis, et al., "Failure of antigen-stimulated gammadelta T cells and CD4+ T cells from sensitized cattle to upregulate nitric oxide and mycobactericidal activity of autologous *Mycobacterium avium* subsp. paratuberculosis-infected macrophages", Veterinary Immunology and Immunopathology vol. 116. No. 1-2., (Feb. 23, 2007), 1-12.

Siziopikou, Kalliopi P, et al., "Augmentation of impaired tumoricidal function in alveolar macrophages from lung cancer patients by cocultivation with allogeneic, but not autologous lymphocytes", Cancer Immunology, Immunotherapy vol. 45. No. 1, (Oct. 1, 1997), 29-36.

Solchaga, Luis A., et al., "Hyaluronic Acid-Based Polymers As Cell Carriers for Tissue-Engineered Repair of Bone and Cartilage", Journal of Orthopaedic Research, Orthopaedic Research Society, US, vol. 17, (Jan. 1, 1999), 205-213.

Sorbera, L A, "Pegsunercept. Pegylated Soluble Tumor Necrosis Factor Receptor Type 1 Peg-Stnf-RI", Drugs of the Future, Prous Science, ES, vol . 28, No. 12, (Jan. 1, 2003), 1182-1188.

Swift, M, et al., "Characterization of Growth Factors in Platelet Rich Plasma", 1-Cell Factor Technologies, [Online]. Retrieved from the Internet: <http://www.cellfactortech.com/global_products.cfm>, (Sep. 16, 2005), 1 pg.

Tateishi-Yuyama, E, et al., "Therapuetic angiogenesis for patients with limb ischaemia by autologous transplantation of bone-barrow cells: a pilot study and randomised controlled trial", The Lancet, (2002), 427-435.

Ulich, Thomas R, et al., "Intratrachael Administration of Endotoxin and Cytokines: IV. The Soluble Tumor Necrosis Factor Receptor Type 1 Inhibits Acute Inflammation", American Journal of Pathology; vol. 142, No. 5, (May 1993).

Vangsness, Thomas, et al., "Stimulation of IL-1ra production from platelet-rich plasma", Poster No. 488 presented at 54th Annual Meeting of the Orthopedic Research Society, (Mar. 2-5, 2008), 1 pg.

Wang, Y, et al., "Ex vivo programmed macrophages ameliorate experimental chronic inflammatory renal disease", Kidney International vol. 72. No. 3, (Apr. 18, 2007), 290-299.

Woodell-May, J, et al., "Effect of Incubation Time on Production of IL-1ra and sTNF-RI from Platelet-Rich Plasma", Paper No. 200, 55th Annual Meeting of the Orthopaedic Research Society, (Feb. 2009).

Woodell-May, J, et al., "Elution of IL-1ra from a concentrated-plasma matrix—An in vitro study", Poster Presentation at 8th World Congress of the International Cartilage Repair Society, (May 2009), 1 pg.

Woodell-May, J, et al., "Producing Accurate Platelet Counts for Platelet Rich Plasma: Validation of a Hematology Analyzer and Preparation Techniques for Counting", Scientific Foundation. Journal of Carniofacial Surgery, vol. 16, No. 5, (Sep. 2005), 749-756.

Woodell-May, Jennifer, et al., "Autologous Protein Solution Inhibits Mmp-13 Production by II-L[Beta] and Tnf[Alpha]-Stimulated Human Articular Chondrocytes", Journal of Orthopaedic Research, vol. 29, No. 9, (Sep. 1, 2011), 1320-1326.

Wright-Carpenter, T, "Treatment of Muscle Injuries by Local Administration of Autologous Conditioned Serum: A Pilot Study on Sportsmen with Muscle Strains", Int J Sports Med, vol. 25, (Oct. 2004), 588-593.

Yang, et al., "Protective effects of IL -1Ra or vIL-10 gene transfer on a murine model of wear debris-included osteolysis", Gene Therapy 11, (2004), 483-491.

Yang, T, et al., "Recent Applications of Polyacrylamide as Biomaterials", Recent Patents on Materials Science, vol. 1, (2008), 29-40.

Yi, Shounan, et al., "IFN-g but not IL-4 is important for mouse CD4+ T cell-mediated macrophage activation following their exposure to pig cells in vitro", Xenotransplantation, vol. 9, No. 4, (Jul. 1, 2002), 268-276.

Yoshida, S, et al., "Elevation of serum soluble tumour necrosis factor (TNF) receptor and IL-1 receptor antagonist levels in bronchial asthma", Clinical and Experimental Immunology, Wiley-Blackwell Publishing Ltd. vol. 106, No. 1, (Oct. 1, 1996), 73-78.

Zhang, et al., "IL-1ra alleviates inflammatory hyperalgesia through preventing phosphorylation of NMDA receptor NR-1 subunit in rats", Pain, vol. 135, No. 3, (Mar. 5, 2008), 232-239.

"European Application Serial No. 14812109.8, Communication Pursuant to Article 94(3) EPC dated Apr. 9, 2018", 5 pgs.

"European Application Serial No. 14812109.8, Response filed Feb. 28, 2018 to Communication Pursuant to Article 94(3) EPC dated Oct. 20, 2017", 14 pgs.

"European Application Serial No. 14812109.8, Communication Pursuant to Article 94(3) EPC dated Jun. 25, 2019", 4 pgs.

"European Application Serial No. 14812109.8, Response filed Apr. 4, 2019 to Communication Pursuant to Article 94(3) EPC dated Oct. 31, 2018", 15 pgs.

"European Application Serial No. 14812109.8, Communication Pursuant to Article 94(3) EPC dated Oct. 31, 2018", 5 pgs.

"European Application Serial No. 14812109.8, Response filed Oct. 10, 2018 to Communication Pursuant to Article 94(3) EPC dated Apr. 9, 2018", 15 pgs.

"European Application No. 14812109.8, Response filed Jan. 3, 2020 to Communication Pursuant to Article 94(3) EPC dated Jun. 25, 2019", 11 pgs.

"European Application Serial No. 14812109.8, Communication Pursuant to Article 94(3) EPC dated Mar. 24, 2020", 4 pgs.

"European Application Serial No. 14812109.8, Response to Communication Pursuant to Article 94(3) EPC dated Jul. 21, 2020", 41 pgs.

(56) References Cited

OTHER PUBLICATIONS

"European Application Serial No. 14812109.8, Communication Pursuant to Article 94(3) EPC dated Jul. 31, 2020", 3 pages.

* cited by examiner

METHODS OF MEDIATING MACROPHAGE PHENOTYPES

RELATED APPLICATIONS

This application is a divisional application of U.S. patent application Ser. No. 14/554,381, filed on Nov. 26, 2016, issued as U.S. Pat. No. 9,833,474 on Dec. 5, 2017, which claims the benefit of priority of U.S. Provisional Patent Application Ser. No. 61/909,249, filed on Nov. 26, 2013, each of which patent disclosures is hereby incorporated by reference in its entirety.

BACKGROUND

Introduction

The present technology relates to methods of inducing polarization of macrophages. For example, methods comprise use of solutions comprising cytokines, including interleukin-4, interleukin-10, and transforming growth factor-beta to induce polarization to an M2 phenotype. Methods also comprise use of platelet-poor plasma to induce polarization to an M1 phenotype.

Macrophages are phagocytes and antigen presenting cells that differentiate from monocytes in circulating peripheral blood. They play an important role in both innate and adaptive immunity by activating T lymphocytes. Macrophages that activate Th1 T lymphocytes provide an inflammatory response and are denoted M1 macrophages. M1 macrophages, also referred to as "killer macrophages," inhibit cell proliferation, cause tissue damage, and are aggressive against bacteria. Macrophages that activate Th2 T lymphocytes provide an anti-inflammatory response and are denoted M2 macrophages. M2 macrophages, also referred to as "repair macrophages," promote cell proliferation and tissue repair and are anti-inflammatory.

Monocytes mature into either M1 (CD 68+ and CD80+) or M2 (CD68+ and CD163+) macrophages depending on the cytokines and growth factors that cause them to differentiate. Lipopolysaccharide (LPS) and interferon gamma (IFNγ) activate monocytes to differentiate into M1 macrophages that secrete high levels of interleukin-1 (IL-1) and interleukin-12 (IL-12) and low levels of interleukin-10 (IL-10). Alternatively, interleukin-4 (IL-4). IL-10, interleukin-1 receptor antagonist (IL-1ra) and transforming growth factor beta (TGFβ) activate monocytes to differentiate into M2 macrophages that secrete high levels of IL-10, TGFβ, and insulin-like growth factor 1 (IGF-1) and low levels of IL-12.

In pro-inflammatory environments, such as the synovial space in an osteoarthritic joint, macrophages become polarized to the inflammatory M1 phenotype. In order to reduce the inflammation associated with various disorders or conditions, it would be useful to induce polarization of macrophages into the anti-inflammatory M2 phenotype. By encouraging macrophage differentiation into the M2 phenotype, inflammatory responses can be suppressed and repairing macrophage responses can be promoted.

Inducing an M2 polarization of macrophages is not always beneficial. For example, in cancer, M2 macrophages can induce vascularization in an area of a tumor. Therefore, in such scenarios it would be useful to inhibit the M2 polarization of macrophages and induce the M1 polarization of macrophages, which attack tumor cells.

However, many methods for inducing polarization of macrophages into the M1 or M2 phenotype require recombinant biomolecules, which may present undesirable side effects. Accordingly, there remains a need to develop novel methods for activating macrophages into M1 or M2 phenotypes that improve efficacy and result in reduced side effects.

SUMMARY

The present technology provides methods and therapeutic compositions for inducing a polarization of macrophages. A method for mediating macrophage phenotypes comprises
   (a) obtaining a blood-derived composition; and
   (b) contacting the blood-derived composition with a source of macrophages,
     wherein contacting the blood-derived composition with the source of macrophages induces a polarization of macrophages.

The source of macrophages may be an in vivo tissue at the site of a disorder to be treated in a human or other animal subject. The source may also comprise a culture of macrophages or macrophage-containing tissue, for implantation at the site of a disorder to be treated in a human or other animal subject.

In some embodiments, the blood-derived composition is platelet-poor plasma (PPP), which induces the source of macrophages to polarize into M1 macrophages. In other embodiments, the blood-derived composition is whole blood or a protein solution, which may be blood derived, comprising interleukin-4, interleukin-10, IL-1ra, and TGFβ. The protein solution induces the source of macrophages to polarize into M2 macrophages. The protein solution may be an autologous protein solution (APS), derived from blood obtained from the subject to be treated with the M2 macrophages.

The present technology further provides methods and therapeutic compositions for the treatment of various disorders, including cancer and other disorders associated with cell proliferation, by inducing an M1 polarization of macrophages at the site of the disorder. Methods include those comprising administering a blood-derived composition to the site of a tumor or to another source of macrophages, wherein the blood-derived composition comprises PPP. A method of inducing monocytes to polarize into M1 macrophages comprises:
   (a) fractionating whole blood into platelet-poor plasma (PPP); and
   (b) contacting the platelet-poor plasma with monocytes, wherein the PPP induces the monocytes to polarize into M1 macrophages. In some embodiments, the method further comprises concentrating the PPP to generate concentrated PPP. The concentrated PPP is then contacted with the monocytes. In other embodiments, the PPP is present as a 25% supplement in a defined culture medium.

The present technology also provides methods and therapeutic compositions for inducing an M2 polarization of macrophages for the treatment of inflammatory disorders or tissue repair. Methods include those comprising administering a blood-derived composition to the site of the inflammation or to another source of macrophages, the composition comprising proteins selected from the group consisting of interleukin-4, interleukin-10, IL-1ra, and TGFβ, wherein the concentration of each protein in the composition is greater than the concentration of the protein in normal blood. In some embodiments, the compositions further comprises a protein selected from the group consisting of sTNF-RII, IGF-I, EGF, HGF, PDGF-AB, PDGF-BB, VEGF, and sIL-1RII, and mixtures thereof, wherein the concentration of the protein in the composition is greater than the concentration of the protein in normal blood. The compositions may also comprise white blood cells, platelets, concentrated plasma, bone marrow aspirate, adipose tissue and combinations thereof. The protein solutions may be made by:
(a) obtaining a cytokine cell suspension from the subject; and
(b) fractionating the cytokine cell suspension to produce an autologous protein solution comprising interleukin-4, interleukin-10, IL-1ra, and TGFβ.

The composition may then be administered to the site of inflammation in a human or other animal subject. The cytokine cell suspension may comprise whole blood, bone marrow aspirate, adipose tissue, urine, fractions thereof, and mixtures thereof. For example, fractionating may comprise placing blood in a container a separator operable to separate the blood into two or more fractions; and centrifuging the separator to create a platelet-rich plasma fraction. The platelet-rich plasma may be contacted with a solid extraction material, such as polyacrylamide beads, to form the autologous protein solution.

Figure 1:
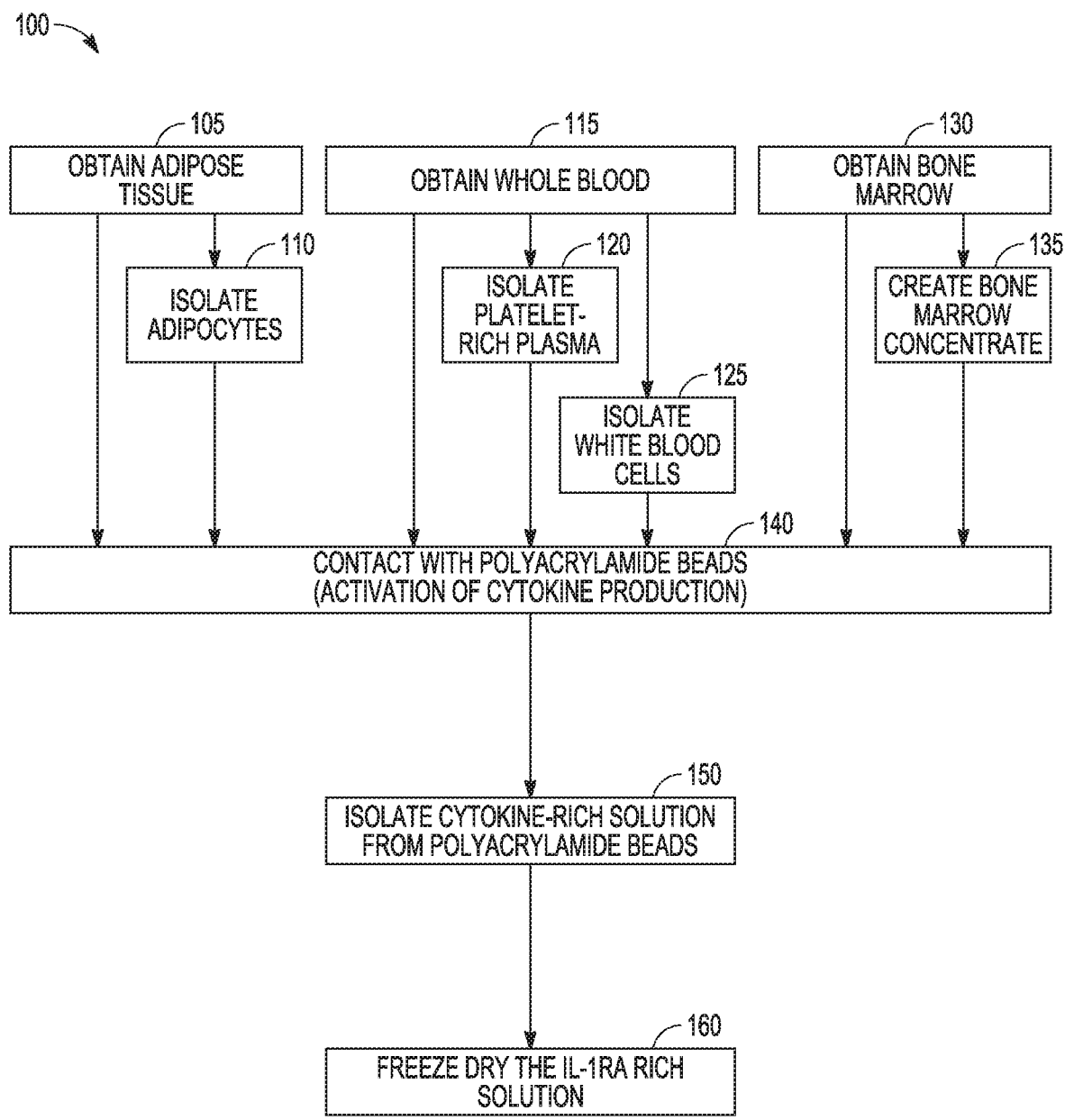
FIG. 1 is a block diagram illustrating a method for producing an anti-inflammatory cytokine composition.

Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments. These figures may not precisely reflect the characteristics of any given embodiment, and are not necessarily intended to fully define or limit specific embodiments within the scope of this technology.

DETAILED DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

It has been discovered that macrophage phenotypes can be mediated by blood fractions. That is, monocytes can be polarized into M1 or M2 macrophages with various blood-derived compositions. In various embodiments, the present technology relates to inducing M2 polarization of macrophages using compositions comprising proteins, including IL-4, IL-10, IL-1ra, TGFβ, and other cytokines. Inducing M2 polarization of macrophages is useful for treating various inflammatory disorders in humans and non-human mammals. In various embodiments, methods for inducing M2 polarization of macrophages from a mammalian subject, comprise:
(a) obtaining a cytokine cell suspension from one or more mammalian subjects;
(b) fractionating the cytokine cell suspension to produce a protein solution comprising one or more proteins, such as IL-4, IL-10, IL-1ra, and TGFβ; and
(c) administering the protein solution to a source of macrophages.

Additionally, the present technology relates to inducing M1 polarization of macrophages using blood derived compositions, such as platelet-poor plasma (PPP).

Protein Compositions

The present technology provides methods for inducing M2 polarization of macrophages in humans or other mammalian subjects using compositions (herein referred to as "Protein Solutions") comprising proteins dissolved, suspended or otherwise carried for delivery to a mammalian subject in a physiologically-acceptable medium. In various embodiments, such compositions comprise proteins (e.g., cytokines) that are native to whole blood in normal mammal subjects. Such compositions may also contain viable cells, including platelets, white blood cells, and combinations thereof. In some embodiments, the medium may be a concentrated plasma solution.

In various embodiments, the Protein Solution comprises at least two proteins selected from the group consisting of IL-1ra (interleukin-1 receptor antagonist), sTNF-RI, sTNF-RII (soluble tumor necrosis factor-receptor 2), interleukin-4 (IL-4), interleukin-10 (IL-10), IGF-1 (insulin-like growth factor 1), EGF (epidermal growth factor), HGF (hepatocyte growth factor), PDGF-AB (platelet-derived growth factor AB), PDGF-BB (platelet-derived growth factor BB), VEGF (vascular endothelial growth factor). TGF-β1 (transforming growth factor-β1), and sIL-1RII (soluble interleukin one receptor II), wherein the concentration of each protein in the composition is greater than the concentration of the protein in normal blood. For the sake of clarity, the Protein Solution may contain three or more of the proteins from the recited group. While the concentration of every such protein in the composition may be greater than its respective concentrations in normal blood, it is not necessary that the concentration of more than two of the proteins be greater than their respective concentrations in normal blood.

In various embodiments, the platelet-rich protein solution comprises the following components.

TABLE 1

Protein Solution Exemplary Protein Components

| Component | Composition Concentration | Normal Whole Blood Concentration |
| --- | --- | --- |
| plasma proteins (total) | about 80 mg/ml or greater<br>about 100 mg/ml or greater<br>about 200 mg/ml or greater<br>about 250 mg/ml or greater | about 67 mg/ml |
| albumin | about 60 mg/ml or greater<br>about 100 mg/ml or greater | about 56 mg/ml |
| fibrinogen | about 3.2 mg/ml or greater<br>about 4 mg/ml or greater | about 2.9 mg/ml |
| IL-1ra | about 10,000 pg/ml or greater<br>about 25,000 pg/ml or greater | about 4200 pg/ml |

TABLE 1-continued

Protein Solution Exemplary Protein Components

| | Composition Concentration | Normal Whole Blood Concentration |
|---|---|---|
| | about 30,000 pg/ml or greater from about 25,000 to about 110,000 pg/ml from about 25,000 to about 40,000 pg/ml | |
| IL-4 | about 5 pg/ml or greater about 10 pg/ml or greater about 20 pg/ml or greater | about 0 pg/ml |
| IL-10 | about 2 pg/ml or greater about 5 pg/ml or greater | about 1 pg/ml |
| sTNF-RI | about 1,200 pg/ml or greater about 1,800 pg/ml or greater about 3,000 pg/ml or greater | about 630 pg/ml |
| sTNF-RII | about 3,000 pg/ml or greater about 5,000 pg/ml or greater about 7,000 pg/ml or greater about 9,000 pg/ml or greater | about 1200 pg/ml |
| sIL-1RII | about 15,000 pg/ml or greater about 20,000 pg/ml or greater about 25,000 pg/ml or greater | about 11,800 pg/ml |
| Growth factors | | |
| EGF | about 800 pg/ml or greater about 1,000 pg/ml or greater about 1,200 pg/ml or greater | about 250 pg/ml |
| HGF | about 1,000 pg/ml or greater about 2,500 pg/ml or greater about 2,800 pg/ml or greater about 3,000 pg/ml or greater | about 500 pg/ml |
| PDGF-AB | about 35,000 pg/ml or greater about 50,000 pg/ml or greater about 70,000 pg/ml or greater | about 6,000 pg/ml |
| PDGF-BB | about 10,000 pg/ml or greater about 15,000 pg/ml or greater about 20,000 pg/ml or greater | about 1,500 pg/ml |
| TGF-β1 | about 100,000 pg/ml or greater about 150,000 pg/ml or greater about 190,000 pg/ml or greater | about 10,000 pg/ml |
| IGF-1 | about 130,000 pg/ml or greater about 150,000 pg/ml or greater about 160,000 pg/ml or greater | about 70,000 pg/ml |
| VEGF | about 500 pg/ml or greater about 600 pg/ml or greater about 800 pg/ml or greater | about 150 pg/ml |

Protein concentrations can be measured using the methods set forth in Example 4.

The composition further preferably comprises viable white blood cells, lysed white blood cells, or both. In a preferred composition, the Protein Solution comprises monocytes, granulocytes, and platelets. In various embodiments, a Protein Solution comprises the following components.

TABLE 2

Protein Solution Exemplary Cellular Components

| Component | Composition Concentration | Normal Whole Blood Concentration |
|---|---|---|
| white blood cells | at least about 15 k/µl at least about 30 k/µl from about 30 to about 60 k/µl from about 40 to about 50 k/µl | 6.5 k/µl |
| red blood cells | less than about 3 M/µl less than about 2 M/µl less than about 2.5 M/µl | 4.5 M/µl |
| Platelets | at least about 400 k/µl at least about 800 k/µl at least about 1,000 k/µl | 240 k/µl |
| Neutrophils | at least about 5 k/µl at least about 10 k/µl at least about 12 k/µl | 3.7 k/µl |
| Monocytes | at least about 1 k/µl at least about 2 k/µl at least about 3 k/µl | 0.5 k/µl |
| Lymphocytes | at least about 5 k/µl at least about 10 k/µl at least about 20 k/µl | 2 k/µl |
| Eosinophiles | at least about 0.15 k/µl at least about 0.18 k/µl | 0.1 k/µl |
| Basophils | at least about 0.2 k/µl at least about 0.4 k/µl at least about 0.6 k/µl | 0.1 k/µl |

It will be understood that concentrations may be species specific, and may vary among individual subjects. Thus, in methods comprising production of a Protein Solution from the blood or other tissue containing cytokine-producing cells, the concentration of proteins and cells in the Protein Solution may vary from those recited above; for example, the values recited above are mean values for concentrations as may be seen in a population of human subjects.

In various embodiments, the concentration of one or more of the proteins or other components in the Protein Solution is greater than the concentration of the component in normal blood. (Compositions with such higher concentrations of components are said to be "rich" in such components.) As referred to herein, the concentration of a component in "normal" blood or other tissue is the concentration found in the general population of mammalian subjects from which the tissue is obtained, e.g., in normal whole blood. In methods wherein the anti-inflammatory cytokine composition is derived from tissue from a specific subject, the "normal" concentration of a protein or cell may be the concentration in the blood of that individual before processing is performed to derive the protein or cell.

Thus, in various embodiments, the concentration of one or more components of the Protein Solution is greater than about 1.5 times, about 2 times, or about 3 times, greater than the concentration of the component in normal blood. For example, components may have greater concentrations in the compositions, relative to normal (whole) blood, as follows:

IL-1ra, at a concentration that is at least about 2.5, or at least about 3 or at least about 5, times greater;
IL-4, at a concentration that is at least about 2.5, or at least about 3 or at least about 5, times greater,
IL-10, at a concentration that is at least about 1.5, or at least about 2 or at least about 2.5, times greater;
sTNF-RI, at a concentration that is at least about 2, or at least about 2.5 or at least about 3, times greater;
sTNF-RII, at a concentration that is at least about 2, or at least about 2.5 or at least about 3, times greater;
sIL-RII, at a concentration that is at least about 1.5, or at least about 1.8 or at least about 2, times greater;
EGF, at a concentration that is at least about 2, or at least about 3 or at least about 5, times greater,
HGF, at a concentration that is at least about 2, or at least about 3 or at least about 4, times greater;
PDGF-AB, at a concentration that is at least about 2, or at least about 3 or at least about 5, times greater;
PDGF-BB, at a concentration that is at least about 2, or at least about 3 or at least about 5, times greater;

TGF-β1, at a concentration that is at least about 3, or at least about 4 or at least about 6, times greater;

IGF-1, at a concentration that is at least about 1.2, or at least about 1.4 or at least about 1.5, times greater, VEGF, at a concentration that is at least about 2, or at least about 2.5 or at least about 3, times greater;

white blood cells, at a concentration that is at least about 2, or at least about 3 or at least about 4, times greater;

platelets, at a concentration that is at least about 2, or at least about 3 or at least 4, times greater, neutrophils, at a concentration that is at least 1.5, or at least 2 or at least 3, times greater;

monocytes, at a concentration that is at least 3, or at least 4 or at least 6, times greater;

lymphocytes, at a concentration that is at least 5, or at least 8 or at least 10, times greater; and basophils, at a concentration that is at least 2, or at least 4 or at least 6, times greater.

Also, the concentration of erythrocytes in the Protein Solution is preferably at least half, or at least a third, of the concentration of erythrocytes in normal blood.

For example, a Protein Solution may comprise:
(a) at least about 10,000 pg/ml IL1-ra;
(b) at least about 1,200 pg/ml sTNF-RI; and
(c) a protein selected from the group consisting of sTNF-RII, IGF-I, EGF, HGF, PDGF-AB, PDGF-BB, VEGF, TGF-β1, and sIL-1RII, and mixtures thereof, wherein the protein has a concentration higher than the protein's baseline concentration in normal blood. In another example, a Protein Solution comprises:
(a) interleukin-1 receptor antagonist (IL-1ra), at a concentration at least 3 times greater than the concentration of IL-1ra in normal blood;
(b) soluble tissue necrosis factor-r1 (sTNF-r1), at a concentration at least 2 times greater than the concentration of IL-1ra in normal blood;
(c) white blood cells at a concentration at least 2 times greater than the concentration of white blood cells in normal blood; and
(d) platelets, at a concentration at least 2 times greater than the concentration of platelets in normal blood.

In some embodiments, the concentration of IL-1ra in the Protein Solution is preferably at least 5.000, or at least 10,000, times greater than the concentration of interleukin-1a in the Protein Solution. The ratio of IL-1ra:interleukin-1β (IL-1β) concentrations is preferably at least 100. In some embodiments, the concentration of IL-1ra in the Protein Solution is preferably at least 1500, or at least 8000, times greater than the concentration of IL-1β in the Protein Solution. The ratio of sIL-1RII:interleukin-1β (IL-1β) concentrations is preferably greater than 1. In some embodiments, the sIL-1RII in the Protein Solution is preferably at least 2000, or at least 45000, times greater the concentration of interleukin-1β in the Protein Solution.

In various embodiments, the Protein Solution comprises one or more components (e.g., platelets) derived from the subject to whom the solution is to be administered in a treatment methods according to this technology. Such components are, accordingly, "autologous." In some embodiments, the Protein Solutions (e.g., Autologous Protein Solutions) consisting essentially of such autologous components. In other embodiments, one or more components of the solution may be obtained from non-autologous sources, such as through recombinant or synthetic methods, or by isolation from allogeneic sources (i.e., from subjects of the same species as the subject to whom the solution is to be administered) or xenogeneic sources (i.e., from animal sources other than the species to whom the solution is to be administered).

Methods of Making Protein Solutions

Protein Solutions may be made by any of a variety of methods, including admixture of individual components and processes wherein one or more components are derived from a source material. In various embodiments, the Protein Solution is made by fractionating a cytokine cell suspension, to produce a protein solution comprising IL1-ra.

Obtaining Protein Solutions by Contacting Cytokine-Producing Cells with an Extraction Material In various embodiments. Protein Solutions are made by derivation of one or more components from tissue comprising cytokine-producing cells. As referred to herein, a "cytokine producing tissue" is a tissue obtained from a mammalian subject, comprising cells that are capable of producing cytokines. Such cells include white blood cells, adipose stromal cells, bone marrow stromal cells, and combinations thereof. It is understood that white blood cells include monocytes, lymphocytes, and granulocytes such as neutrophils, eosinophils, and basophils. White blood cell useful in the methods of this technology preferably include monocytes and neutrophils. Cytokine producing tissues among those useful herein include blood, adipose tissue, bone marrow, and fractions thereof, as further discussed below.

Blood useful herein includes whole blood, plasma, platelet-rich plasma, platelet-poor plasma, and blot clots. In a preferred embodiment, methods of the present technology use platelet-rich plasma (PRP), containing white blood cells and platelets, comprising the buffy coat layer created by sedimentation of whole blood. Adipose tissue useful herein includes any fat tissue, including white and brown adipose tissue, which may be derived from subcutaneous, omental/visceral, mammary, gonadal, or other adipose tissue sites. Bone marrow useful herein includes red marrow and yellow marrow. In a preferred embodiment, bone marrow is bone marrow concentrate, obtained from the red marrow of long bones, comprising hematopoietic and mesenchymal stems cells. As discussed above, blood, adipose, and bone marrow tissue useful herein may be from either autologous or allogeneic sources, relative to the subject to be treated according to methods of this technology. Compositions may also be made from combinations of allogeneic and autologous tissues.

In some embodiments, methods comprise fractionating a liquid (a "cytokine cell suspension") comprising cells capable of producing cytokines, such as IL1-ra and sTNF-R1. As discussed above, such cells include white blood cells, adipose stromal cells, bone marrow stromal cells, and combinations thereof. In some embodiments, the cytokine cell suspension is a liquid comprising white blood cells. It should be understood that the cytokine cell suspension comprises cells and an extra-cellular liquid, regardless of the relative proportions of the cells and liquid. In some embodiments, the suspension may comprise primarily cells, with liquid being present as only a minor component, essentially wetting the cells. In some embodiments, the liquid may comprise two phases, consisting of a phase primarily consisting of liquid and a phase primarily consisting of cells, forming a suspension of cells in the liquid only upon agitation or other mixing.

In some embodiments, fractionating a cytokine cell suspension comprises contacting the liquid with a solid extraction material. As exemplified in FIG. 1, such processes comprise:

(a) obtaining a cytokine cell suspension, such as a liquid comprising white blood cells (steps 105, 115 or 135, or combinations thereof);

(b) contacting the tissue with a solid extraction material (step 140); and (c) isolating a protein-containing liquid from the solid extraction material (step 150).

Obtaining the suspension 105, 115, 135 can comprise any of a variety of methods for creating a liquid containing cells among those known in the art. Such methods include isolation from tissue and culturing. Obtaining may be performed directly in the method, whereby a health care practitioner or other individual performs isolation, processing, culturing or other processes for creating the suspension, in a procedure that includes the contacting and isolating steps. In some embodiments, the processes for creating the suspension are performed contemporaneously with the contacting and isolating steps, as part of a point-of-care procedure, as discussed further herein. Alternatively, obtaining the suspension may be indirect, involving only the acquisition of the suspension for use in the contacting and isolating steps, wherein the processing to create the suspension has previously been performed by another party.

In various embodiments, obtaining comprises isolating a cytokine cell suspension, comprising white blood cells or other cytokine-producing cells, from blood, adipose tissue, bone marrow aspirate or other tissue comprising cytokine-producing cells, as exemplified in Steps 110, 120 and 125 of FIG. 1. Methods may comprise obtaining a cytokine cell suspension from two, three or more tissue sources.

Obtaining a Cytokine Cell Suspension from Blood

In embodiments comprising the use of blood, the blood may be used directly in contacting the solid extraction material, as exemplified in step 140 of FIG. 1, or may be processed to provide a blood fraction, such as PRP, in a preferred embodiment. Many devices and methods for creating blood fractions are known in the art, using such means as centrifugation and filtering.

In various embodiments, methods of the present technology comprise creating PRP as the cytokine cell suspension, using centrifugation. Such methods generally comprise placing blood in a container a separator operable to separate the blood into two or more fractions, and centrifuging the separator to create a platelet-rich plasma fraction. Such devices may include a tube and a buoy disposed in the tube, wherein the buoy has a density such that the buoy reaches an equilibrium position upon centrifugation of the tissue in the tube, the equilibrium position being between a first fraction and a second fraction comprising cytokine-producing cells, the second fraction having a concentration of cytokine-producing cells greater than the concentration of cytokine-producing cells in the first fraction. Such methods further comprise centrifuging the tube so that the buoy defines an interface between the first fraction and the second fraction comprising cytokine-producing cells. The second fraction is then collected for further use in the methods of this technology.

One such device useful herein is described in U.S. Pat. No. 7,992,725, Leach et al., issued Aug. 9, 2011. Such a device is commercially available as GPS III Platelet Concentrate and Separation System, from Biomet Biologics, LLC (Warsaw, Ind., USA). The device can be used in a clinical or laboratory environment to isolate fractions from a suspension or multi-component tissue material obtained from a subject, such as blood, bone marrow aspirate, cerebrospinal fluid, adipose tissue, Isolated fractions can include platelets, platelet poor plasma, platelet rich plasma and stromal cells. The isolated fractions can each have equilibrium point or positions within the separation container that are achieved when separation has occurred. For example, a buffy coat (PRP) of whole blood may have an equilibrium position above that of the red blood cells when a sample of whole blood is separated.

Figure 2:
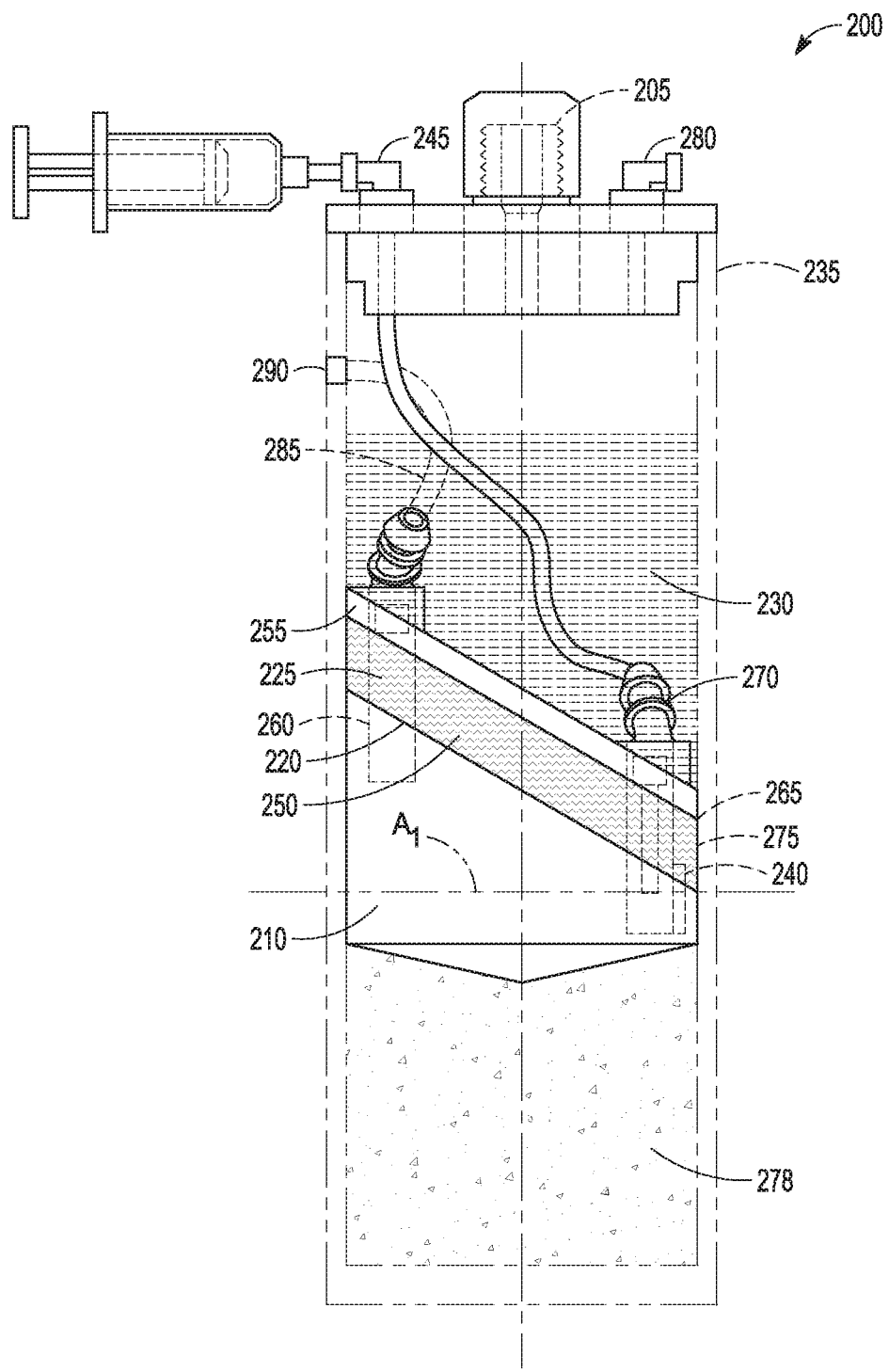
FIG. 2 is a diagram of a fractionation device.

The fractionation device 200 is exemplified in FIG. 2. The fractionation device 200 comprises a buoy 210 and a container wall 215. When the separation container 205 is centrifuged, the buoy perimeter 210a and the container wall 215 have clearance allowing the buoy 210 to move within the separation container 205 and a material to pass between the buoy perimeter 210a and the container wall 215. Alternatively, the buoy 210 could have an opening, such as a centrally or internally located opening or a peripheral channel running the height of the buoy, which would allow a material to move through the buoy.

The buoy 210 is carried in the separation container 205 and has a tuned density that is configured to reach a selected equilibrium position in a suspension. The buoy can have its density tuned in the range from about 1.0 g/cc to about 1.10 g/cc, such as about 1.06 g/cc. The buoy 210, according to various embodiments, can be formed to include the tuned density and can be formed of one or more materials to achieve the tuned density.

Referring to FIG. 2, a collection area 220 is positioned within the device 200 after a separation procedure has occurred. The collection area 220, defined relative to the buoy 210, is positioned at an equilibrium position of a separated or isolated middle fraction 225 in the container. The equilibrium position of a selected fraction can be defined as its position within the container relative to other fractions in the container of a separated sample or material. The equilibrium position can also be defined relative to the axis X of the buoy 210 or the container 12. The equilibrium position, however, may depend upon the amount of the sample of the amount of a selected fraction within a sample. According to the illustration in FIG. 2, the equilibrium position of the fraction 230 is above or nearer a top 235 of the device 200 than the equilibrium position of the fraction 225. Thus, the buoy 210 can be tuned, such as including a selected density or specific gravity, to position the collection area 220 relative to an equilibrium position of any selected fraction.

In some embodiments, the buoy 210 can comprise a collection port 240. The collection port 240 communicates with access port 245 and communicates with a collection space 220 above buoy upper surface 250 and can be located near the buoy perimeter 210a. In some embodiments, the collection port 240 is not carried on the buoy, but rather the collection port is a withdraw device such as a syringe that is inserted through an access port or top of the device 200.

According to various embodiments, an isolator 255, is coupled to the buoy 210. The combination of the isolator and buoy, according to various embodiments, can also be referred to as a separation assembly member. The isolator 255, for example, provides a means for creating the collection compartment 220 and comprises one or more spacers 260, 265 to position the isolator 255 apart from the buoy 210 to create the collection compartment 220. A withdraw port 270 can be carried on the isolator 255 communicating with the withdraw port 245 and the collection port 240. The spacer 260, 265 can also serve as a conduit 275 between the collection port 50 and a withdraw or withdraw port 245. The withdraw port 245 serves as a structure for withdrawing the isolated or second fraction 310 from the collection compartment 220.

After centrifuging the device 200 containing whole blood, the first fraction or top fraction 230, can be platelet-poor-plasma, the middle fraction 225 can be platelet-rich plasma or platelet concentrate, and a bottom fraction 278 can be red blood cells. Therefore, the fractionation method further comprises withdrawing a desired fraction from the device 200. Various ports 205, 245 and 280 can be provided to allow access to any appropriate compartment of the device 200. The access ports 205, 245, 280 can be any means that allow communication from outside the separation device 200 to the device's interior, such as a Luer lock port, a septum, a valve, or other opening. Additionally, collection vent tube 285 allows removal of a fractionated suspension in the collection area 220 through opening 290 without the need to remove the fraction, such as plasma, above the isolator 255. Although, without a collection vent tube 285, the fraction above the isolator could be removed and the collection area could be vented to the area above the isolator.

A method for using the fractionation device 200 can begin by inputting whole blood via an access port 205. The fractionation device 200 is placed into a centrifuge and spun for a period that is appropriate for fractionating whole blood. An exemplary period can be for about five minutes to about twenty minutes at a rate of about 320 rpm to about 5000 rpm. This speed may produce a selected gravity that may be approximately 7.17×g to about 1750×g (times greater than the normal force of gravity).

Other devices that may be used to isolate platelet-rich plasma are described, for example, in U.S. Pat. No. 5,585,007, Antanavich, issued Dec. 17, 1996; U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Pat. No. 7,179,391, Leach et al., issued Feb. 20, 2007; U.S. Pat. No. 7,374,678, Leach et al., issued May 20, 2008; U.S. Pat. No. 7,223,346, Dorian et al., issued May 29, 2007; and U.S. Pat. No. 7,708,152, Dorian et al., issued May 4, 2010.

In addition to the GPS® Platelet Concentrate and Separation Systems, a variety of other commercially available devices may be used to isolate platelet-rich plasma, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); the AutoloGel™ Process, commercially available from Cytomedix, Inc. (Rockville, Md., USA); the GenesisCS System, commercially available from EmCyte Corporation (Fort Myers, Fla., USA); the PCCS System, commercially available from Biomet 3i, Inc. (Palm Beach Gardens, Fla., USA); and the Arthrex ACP™ Double Syringe System, commercially available from Arthrex, Inc. (Naples, Fla. USA).

Referring again to FIG. 1, blood drawn from the patient may be mixed with an anticoagulant in one or more of Steps 115, 120, 125, and 130, so as to facilitate processing. Suitable anticoagulants include heparin, citrate phosphate dextrose (CPD), ethylenediaminetetraacetic acid (EDTA), anticoagulant citrate dextrose solution (ACD), and mixtures thereof. For example, the anticoagulant may be placed in the syringe used for drawing blood from the subject, or may be mixed with the blood after it is drawn.

A cytokine cell suspension may be prepared by admixing cells with a suitable liquid, as shown in step 125, using methods known in the art. For example, white blood cells may be isolated from whole blood by lysing red blood cells or by centrifugation of whole blood utilizing a density gradient where the white blood cells sediment to the bottom of a centrifuge tube. An example of density centrifugation includes the Ficoll-Paque™ Plus (GE Healthcare Bio-Sciences, Piscataway, N.J., USA). In some cases, a density gradient may be used to further separate mononuclear and polymorphonuclear cells. Cytokine-producing cells may also be prepared from whole blood using filtration; an example includes the Acelere™ MNC Harvest System (Pall Life Sciences. Ann Arbor, Mich., USA). Cytokine-producing cells can also be obtained from bone marrow. The cytokine-producing cells may be then suspended in a suitable medium, such as plasma, so as to maintain their viability.

Other methods may be used to create platelet-rich plasma or other cytokine cell suspension. For example, whole blood can be centrifuged without using a buoy system, whole blood may be centrifuged in multiple stages, continuous-flow centrifugation can be used, and filtration can also be used. In addition, a blood component including platelet-rich plasma can be produced by separating plasma from red blood cells using a slow speed centrifugation step to prevent pelleting of the platelets. In other embodiments, the buffy coat fraction formed from centrifuged blood can be separated from remaining plasma and re-suspended to form platelet-rich plasma.

Obtaining a Cytokine Cell Suspension from Adipose Tissue

In embodiments comprising the use of adipose tissue, the adipose tissue may be used directly in contacting the solid extraction material, as exemplified in step 140 of FIG. 1, or the adipose tissue may be processed to provide isolated adipocytes in step 110. Cell fractions comprising adipose-derived stem cells are also useful in this method. In some embodiments, adipose tissue is derived from human subcutaneous fat isolated by suction assisted lipectomy or liposuction. Stromal cells may be isolated from the adipose tissue and/or tissue portions using any suitable method, including methods known in the art such as mechanical and breakdown centrifugation. Stromal cells can also be isolated using enzymatic digestion. For example, stromal cells can be isolated from lipoaspirate, treated by sonication and/or enzymatic digestion, and enriched by centrifugation. Stromal cells isolated from adipose tissue may be washed and pelleted.

For example, adipose tissue can be collected by suction-assisted tumescent liposuction inside a specialized collection container attached to suction hoses and to a liposuction cannula. The collection container can have a gauze-type grid filter that allows the tumescent fluid to pass through and retains the solid adipose tissue. After collecting the adipose tissue, the collection container is removed from the suction device and reattached to a centrifugation device. The filter unit may further contain a filter having approximately a 100 micrometer pore size. Once the collection container containing the adipose tissue is attached to the centrifugation device, the tissue is sonicated. After sonication, the entire apparatus is inserted into a centrifuge bucket and centrifuged at, for example, 300×g for 5 minutes. After centrifugation, the collection container together with the filter unit is detached and can be discarded. The pellet containing the stromal cells can then be re-suspended in biocompatible solutions, such as plasma, plasma concentrate and platelet-rich plasma.

Various methods and devices for isolating and/or fractionating adipose tissue and adipocytes include those as described by U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276, Leach et al., issued Oct. 5, 2010; and U.S. Pat. No. 8,048,297, Leach et al., issued Nov. 1, 2011. A device, such as the GPS™ Platelet Concentrate System, commercially available from Biomet Biologics, LLC (Warsaw, Ind., USA), may be used to isolate adipocytes.

Obtaining a Cytokine Cell Suspension from Bone Marrow

In embodiments comprising the use of bone marrow, the marrow may be used directly in contacting the solid extraction material, as exemplified in step 140 of FIG. 1, or may be processed to provide a bone marrow concentrate, as in step 135. Many devices and methods for obtaining and concentrating bone marrow are known in the art.

An exemplary process for isolating and creating a bone marrow concentrate (cBMA) is diagrammed in FIG. 6. Generally, the method 600 may start in step 605 with obtaining a bone marrow aspirate volume. The bone marrow aspirate (BMA) may be obtained in any selected or generally known manner. For example, a selected region of bone, such as a portion near an operative procedure, may be used to obtain the bone marrow aspirate. Generally, an accessing device, such as a syringe and needle, may be used to access an intramedullary area of a selected bone. A small volume of the selected portion may be drawn from a plurality of locations to obtain an appropriate volume of BMA or selected fraction of the BMA.

Once a selected volume of the BMA is obtained in step 605, it may be separated and concentrated using a gravimetric separator. Separators among those useful herein are operable to separate a multi-component fluid that generally includes various components or constituents of varying densities that are commingled or mixed together, including those described above for separation of fractions from blood and adipose tissue. The separator may include a buoy that is of a selected density relative to BMA. Such separators include those described above for use in concentrating and isolating fractions from blood and adipose tissue, including those described in U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276. Leach et al., issued Oct. 5, 2010; and U.S. Pat. No. 8,048,297, Leach et al., issued Nov. 1, 2011. A device, such as the GPS™ Platelet Concentrate System, commercially available from Biomet Biologics, LLC (Warsaw, Ind., USA), may be used to isolate adipocytes. Separators and methods that may be used to fractionate BMA at steps 610 and 615 are also described, for example, in U.S. Application Publication No. 2006/0278588, Woodell-May, published Dec. 14, 2006. The BMA may be positioned in a separator according to various embodiments in step 610. Once the BMA is positioned in the separator, a selected fraction of the BMA may be separated from the BMA in step 615.

Once the BMA is placed in the separator, separator is spun in a centrifuge in a range between about 1.000 and about 8,000 RPM. This produces a force between about 65 and about 4500 times greater than the force of normal gravity, as generally calculated in the art, on the separator and the BMA. At this force, the more dense material in a BMA sample is forced toward the bottom end of the tube. The separator can thus be used to remove nucleated cells from the bone marrow sample. In various embodiments, concentrated BMA has a concentration of nucleated cells that is at least 2, at least 3, at least 4, or at least 5 times the concentration of nucleated cells in BMA.

Obtaining a Cytokine Cell Suspension from Blood Clots

In other embodiments comprising the use of blood, a liquid comprising cytokine-producing cells may be trapped in a blood clot. Cell release can be generated from the blood clot by either compression ("squeezing"), clot disruption, or centrifugation. The blood clot can be made with or without anticoagulant and with or without exogenous thrombin by combining blood or a blood fraction with a clotting agent. Suitable clotting agents include thrombin (e.g., bovine, recombinant human, pooled human, or autologous), autologous clotting protein, and polyethylene glycol. Calcium may be in the form of a calcium salt, such as calcium chloride.

In some embodiments, the clotting agent comprises a clotting protein, which may be a clotting fraction derived from a blood obtained from the patient to be treated. A suitable clotting fraction can be obtained by a process of: loading whole blood or plasma with a calcium solution (e.g., calcium chloride in ethanol) into a blood isolation device; optionally heating the whole blood or plasma for at least about 20 minutes, at a temperature of at least about 20° C.; and isolating the clotting fraction. The isolating may be performed by centrifuging the heated whole blood or plasma. A suitable isolation device is commercially available as the Clotalyst™ Autologous Thrombin Collection System (hereinafter "Clotalyst System"), sold by Biomet Biologics LLC, Warsaw, Ind., USA.

Figure 4:
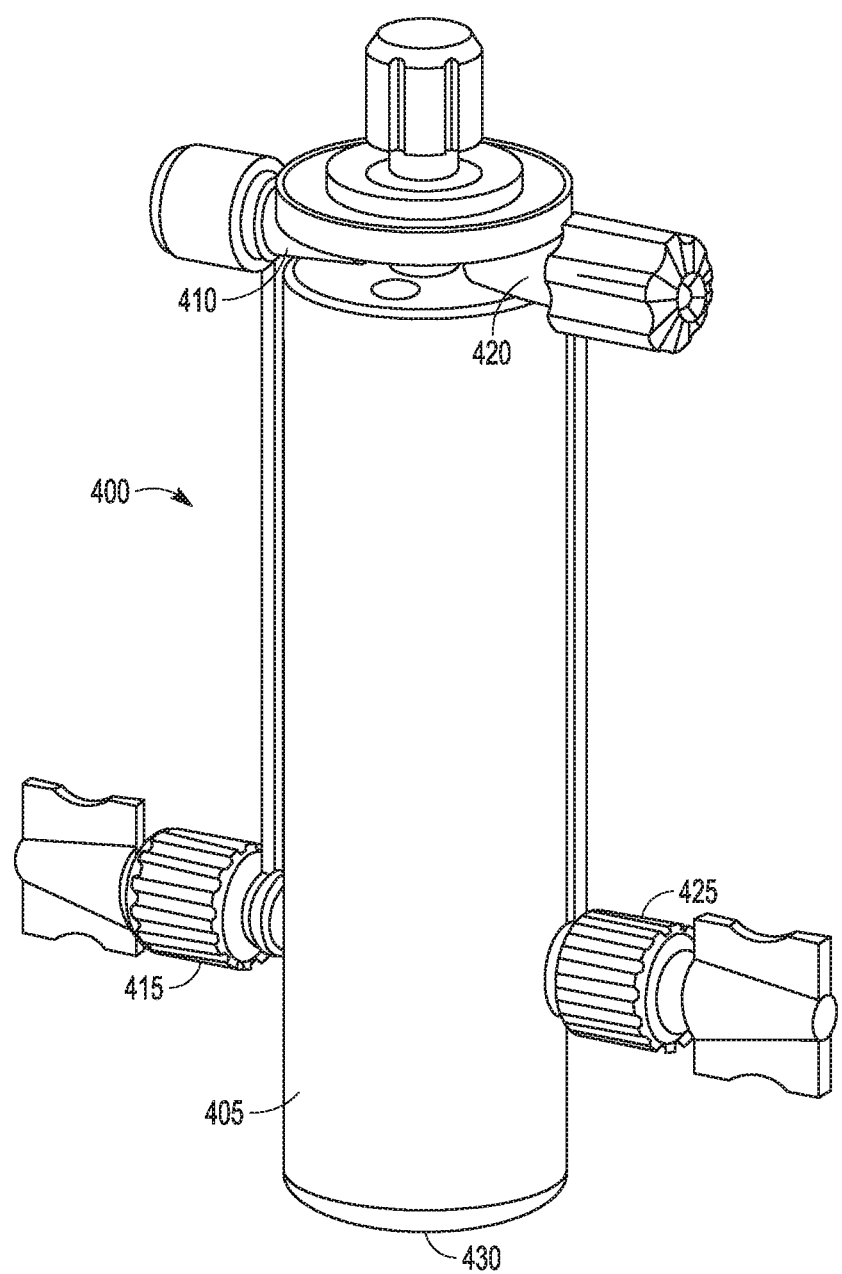
FIG. 4 is a diagram of a device for generating a blood clot.

An exemplary procedure for producing a clotting agent using a device 400 of FIG. 4 begins with injecting a reagent comprising calcium chloride and ethanol into the main chamber 405 through the first port 410. Glass beads are also placed in the main chamber 405. After the reagent has been injected, the first port 410 is closed using the first replacement cap 415. Blood with anticoagulant is injected into the main chamber 405 through the second port 420. After the blood has been injected, the second port 420 is closed using the second replacement cap 425. Optionally, the syringes and blood separation device 400 are pre-heated to a temperature of about 25° C.

The contents of the blood component separation device 400 are mixed by repeatedly inverting the device 400. e.g. about twelve times, so as to contact the blood with the glass beads. After mixing, the device is incubated The incubation process can be at a temperature and for a duration that will permit the contents of the device 400 to be heated at about 25° C. for about 15 minutes. Upon completion of the incubation period, a clotted mass of red blood cells, blood plasma, and glass beads forms at a second end 406 of the main chamber 405. After incubation is complete, the device 400 is shaken enough to dislodge and break-up any gel that may be present.

Obtaining a Cytokine Suspension Using Non-Centrifugal Methods

As noted above, the liquid containing white blood cells can be obtained by non-centrifugal means, such as by culturing. As referred to herein, a "non-centrifugal method" comprises a process for obtaining tissue fractions comprising cytokine-producing cells from tissue without use of a centrifuge. In some embodiments, methods are "non-gravimetric," wherein, based on physical, chemical or physico-chemical properties of the cells other than density, wherein the concentration of white blood cells in the fraction are higher than the concentration of white blood cells in the tissue. Such non-gravimetric methods are, in particular, distinguished from methods wherein a white blood cell fraction is created by centrifugation of whole blood or other tissue. In some embodiments, the non-centrifugal method comprises a process solely based on such properties of white blood cells other than density. Non-centrifugal methods include filtration, antibody binding, and electrophoretic methods.

For example, as discussed above, white blood cells may be prepared from whole blood, bone marrow aspirate or other tissue, using filtration. White blood cells and other cytokine-producing cells obtained from blood, bone marrow, adipose tissue or other sources may also be cultured, using methods among those known in the art. The cells may be then suspended in a suitable medium, such as plasma, so as to maintain their viability and facilitate mixing or other contact with a solid extraction material. A liquid containing the cells may also be produced by compression or disruption of blood clots, as described above.

Contacting a Cytokine Cell Suspension with an Extraction Material and Isolating a Protein Solution In further reference to the exemplified process of FIG. 1, the cytokine cell suspension is incubated or otherwise contacted with a solid extraction material (step 140) to produce a protein-containing liquid. This liquid is then isolated (step 150) from the solid extraction material, as a Protein Solution of the present technology. Without limiting the scope, mechanism or function of the present technology, solid extraction materials useful herein concentrate cytokines or other proteins in the liquid volume of cytokine-producing cells and may, in some embodiments, activate, stimulate or otherwise increase production of cytokines, including IL-1ra. Thus, in some embodiments, methods comprising activating a cytokine cell suspension with a solid extraction material.

The solid extraction material can include various materials that provide a particular surface area to contact the cells. The solid extraction material may be a continuous material or may be discontinuous and comprise a plurality of separate particles. For example, the solid extraction material may be in the form of a plurality of beads, fibers, powder, a porous material, or a surface of a container comprising the liquid containing the cells. The solid extraction material may comprise geometric forms having various cross-sectional shapes, such as spherical, oval, or polygonal, among others. The solid extraction material can also comprise a continuous porous network, similar to a sponge, or can include a plurality of individual porous particles. The solid extraction material may also provide a larger surface area by being porous in comparison to a non-porous material.

In some embodiments, the solid extraction material includes particles having a large aspect ratio, for example, where the particles are needle-like in shape. The solid extraction material may also be formed as long fibers and may be or take a form similar to glass wool.

In some cases, the solid extraction material can comprise the internal walls of a container holding the cytokine cell suspension. For example, the solid extraction material may comprise the lumen of a syringe that contains the cytokine cell suspension. Other containers include tubes, such as centrifuge tubes, or a blood fractionation device or concentrator assembly as described elsewhere herein.

Where the solid extraction material is a continuous material, such as a porous sponge-like material, the solid extraction material can be used in an amount sufficient to absorb or adsorb or include substantially the entire liquid volume of cytokine-producing cells within the pores or interstices of the solid extraction material. Where the solid extraction material is a discontinuous material, such as a plurality of particles, the solid extraction material can be combined with the liquid containing the cells to form a slurry-like composition. The slurry can vary in consistency from paste-like, having a high-solids fraction, to a readily flowable slurry having a low-solids fraction.

The solid extraction material can provide a large surface area with which to contact the cells. However, in some cases, the solid extraction material can be further treated to increase its surface area, for example, by physically or chemically etching or eroding the surface of the solid extraction material. With respect to chemical etching, a corrosive agent can be used to modify the surface of the solid extraction material depending on the nature of the material. The modified surface may be produced by employing an alkali or an acid, for example chromosulphonic acid, in particular about 20% to about 80% in strength, preferably about 50% chromosulphonic acid. The solid extraction material can be incubated with the corrosive agent for about 5 min to about 30 min in order to chemically etch the surface and increase the surface area. The solid extraction material can then be washed to remove the corrosive agent. For example, the solid extraction material can include the internal walls of a container for holding the cytokine cell suspension where the internal walls are etched to subsequently increase the surface area in contact with the liquid.

Various polymers, metals, ceramics, and glasses can be used as the solid extraction material. In some embodiments, the solid extraction material comprises a hygroscopic material. Examples of suitable solid extraction materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose. A preferred solid extraction material comprises, or consists essentially of, polyacrylamide, as further described below.

The solid extraction material may comprise, for example, continuous solid extraction material of glass or a plurality of glass particles, glass wool, a continuous solid extraction material of metal such as titanium, a plurality of metal beads, metal powder, and combinations thereof. A continuous solid extraction material of metal can include a block or other three-dimensional shape formed of porous metal or metal alloys with an open cell structure. The solid extraction material may include various beads or particles of various sizes including substantially spherical beads. Beads include polystyrene beads, polyacrylamide beads, glass beads, metal (e.g., titanium) beads, or any other appropriate beads. Beads may be any size appropriate for the container and the amount of cytokine cell suspension being used. In some instances, bead sizes can range from about 0.001 millimeters to about 3 millimeters in diameter. Where the bead size is sufficiently small, the beads can appear more like a powder.

Polyacrylamide beads used as the solid extraction material can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules. Calif., USA) have particle sizes ranging from less than about 45 µm up to about 180 µm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads (i.e., desiccating polyacrylamide beads) may be used to absorb a portion of a liquid volume, including solutes smaller than the bead pore size, and can serve to concentrate IL-1ra and other proteins produced by the cytokine-producing cells. For example, combining dry polyacrylamide beads with the blood and/or platelet-rich plasma in step 230 activates production of IL-1ra by the cytokine-producing cells and also reduces the total liquid volume as the dry beads rehydrate and swell.

Without limiting the scope, mechanism or function of the present technology, it has been discovered that surface contact with the solid extraction material can activate the cells and the solid extraction material can, in some cases, assist in the separation and concentration of the resulting Protein Solution rich in cytokines, including IL-1ra. For example, in the case of a porous solid extraction material, a portion of the liquid comprising the cells can enter the pores and remain therein. Cells in the liquid may contact this additional surface area. In some embodiments, the pores are too small for the cells to enter, but a portion of the liquid can enter the pores. Liquid can be removed from the solid extraction material and pores by centrifuging, for example.

The solid extraction material is preferably sterilized, using techniques among those known in the art, in order to prevent contamination of the cytokine cell suspension. For example, heat and pressure sterilization methods, such as autoclaving, may be used depending on the particular composition of the solid extraction material. Alternative methods, such as chemical sterilization or irradiation, can be used where the solid extraction material may be adversely affected by the autoclaving process.

In some embodiments, the cytokine cell suspension is incubated with solid extraction material for a time effective to remove a portion of the liquid. The incubation may be carried out over a period from about 30 seconds to about 72 hours and may be carried out at a temperature from about 20° C. to about 41° C. For example, the incubation may be 24 hours or less, 10 hours or less, 5 hours or less, 2 hours or less, 1 hour or less, 30 minutes or less, 15 minutes or less 10 minutes or less, 5 minutes or less, 4 minutes or less, 3 minutes or less, or 2 minutes or less. Incubation may be at least about 15 seconds, at least about 30 seconds, at least about 1 minute, at least about 90 seconds, at least about 2 minutes, at least about 10 minutes, or at least about 30 minutes. In some embodiments, incubations are from about 1 minute to about 3 minutes. In some embodiments the liquid is not incubated, but is contacted with the solid extraction material for only so long as necessary to perform subsequent processing. The contacting may occur at ambient conditions, e.g., at a temperature of about 20-25° C.

In some embodiments, the cytokine cell suspension and the solid extraction material are agitated to more thoroughly mix these components during contact. The agitation may be accomplished by inverting, shaking, rocking, stirring, or vortexing the liquid and solid extraction material. Agitation may increase contact of the cells within the liquid with the solid extraction material. Agitation may be performed once, repeated multiple times, repeated periodically, or may be continuous. The liquid comprising the cells and the solid extraction material may also be agitated while the liquid is stimulated with the electromagnetic field. Additional aspects and features relating to producing protein-rich solutions using polyacrylamide beads and other solid extraction materials are described in: U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561. Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012. Compositions and methods useful in aspects of the present technology are also described in the following applications filed concurrently with this disclosure: U.S. patent application Ser. No. 12/840,562, filed Mar. 15, 2013, Binder et al., Methods and Non-Immunogenic Compositions for Treating Inflammatory Diseases; U.S. patent application Ser. No. 13/841,083, filed Mar. 15, 2013, Landrigan, et al., Treatment of Inflammatory Respiratory Disease Using Protein Solutions; U.S. patent application Ser. No. 13/875,005, filed Mar. 15, 2013, Woodell-May et al., Methods and Acellular Compositions for Treating Inflammatory Disorders; U.S. patent application Ser. No. 13/837,480, filed Mar. 15, 2013, O'Shaughnessey, et al. Treatment of Pain Using Protein Solutions; U.S. patent application Ser. No. 13/839,280, filed Mar. 15, 2013, Leach et al., Methods for Making Cytokine Compositions from Tissue Using Non-Centrifugal Methods; and U.S. patent application Ser. No. 13/840,129, filed on Mar. 15, 2013, Matusuka, et al., Treatment of Collagen Defects Using Protein Solutions, all of which are incorporated by reference herein.

Contacting of the cytokine cell suspension with the solid extraction material may be performed using a suitable container or other apparatus to effect the contact. Contacting may be performed in a continuous process wherein a flow of the liquid is passed over or through the solid extraction material, or the liquid and solid extraction material may be contained in a vessel. As discussed above, the vessel may comprise the solid extraction material, or may merely serve as a container holding the beads or other forms of the material. Containers useful in the present technology include those known in the art, such as the Plasmax™ Plus Plasma Concentrator, commercially available from Biomet Biologics, LLC (Warsaw, Ind. USA) and may include those devices and methods of use as described in U.S. Pat. No. 7,553,413, Dorian et al., issued Jun. 30, 2009; and U.S. Pat. No. 7,694,828, Swift et al., issued Apr. 13, 2010.

Figure 3A:
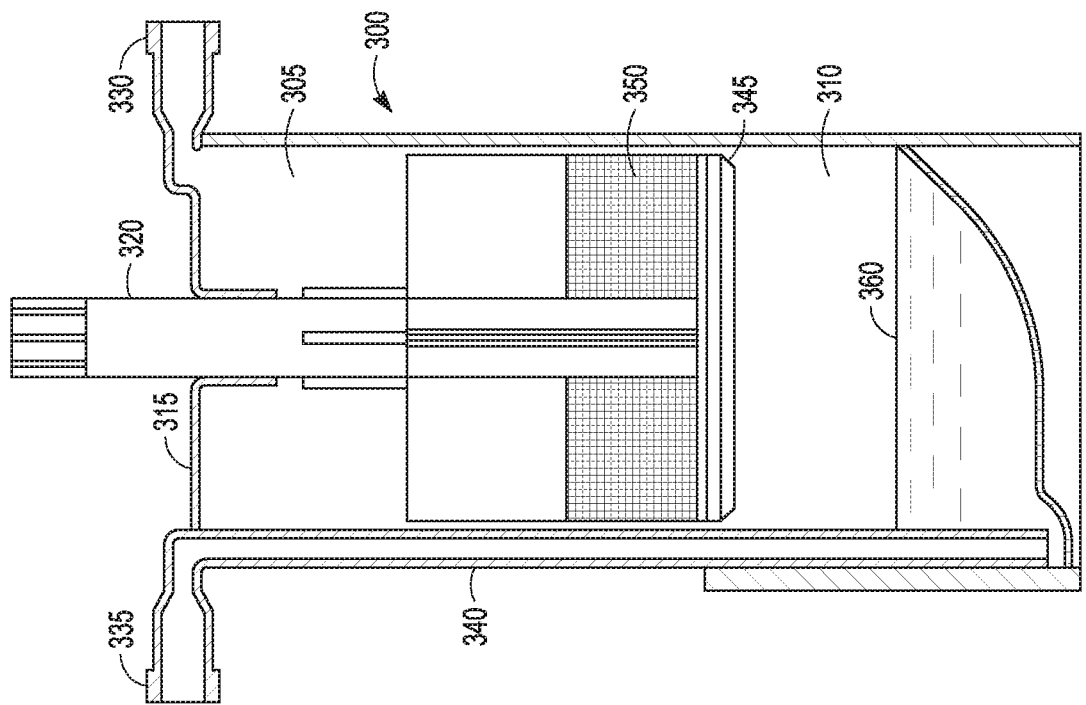
FIG. 3 shows a device for activating a sample to generate anti-inflammatory cytokines, before (FIG. 3A) and after (FIG. 3B) centrifugation.
Figure 3B:
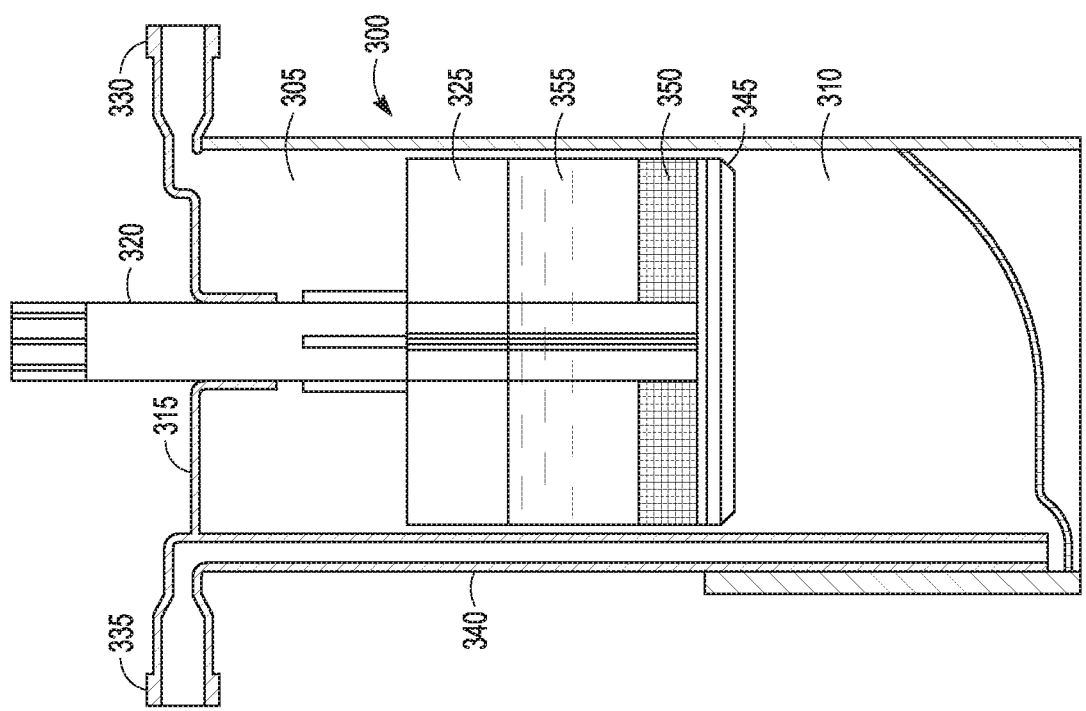

Such a device is shown in FIGS. 3A and 3B, for exemplary use with a polyacrylamide gel bead solid extraction material. The device 300 has an upper chamber 305 and a lower chamber 310. The upper chamber 305 has an end wall 315 through which the agitator stem 320 of a gel bead agitator 325 extends. The device 300 also has an inlet port 330 that extends through the end wall 315 and into the upper chamber 305. The device 300 also includes an outlet port 335 that communicates with a plasma concentrate conduit 340. The floor of upper chamber 305 includes a filter 345, the upper surface of which supports desiccated concentrating polyacrylamide beads 350.

During use, a fluid 355 containing cytokine-producing cells and, optionally, platelets is injected to the upper chamber 305 via the inlet port 330 and mixed with the polyacrylamide beads 350. The fluid 355 and polyacrylamide beads 350 may be mixed by rotating the agitator stem 320 and the gel bead agitator 325, to help mix the fluid 355 and beads 350. The mixed fluid 355 and polyacrylamide beads 350 are then incubated for the desired time at the desired temperature. The device 300 is then centrifuged so that liquid passes to the lower chamber 310 while the polyacrylamide beads 350 are retained by a filter 345, thereby separating the polyacrylamide beads 350 from the resulting solution 360 of IL-1ra and other proteins that collects in the lower chamber 310. The solution 360 may be removed from the device via outlet port 335.

In some embodiments, a Protein Solution can be made in a process wherein a cytokine cell suspension is isolated from a tissue and then contacted with a solid extraction material in a continuous process. Referring again to FIG. 1, in some embodiments the isolating 110, 120, 135 and contacting 140 are performed using a single apparatus, referred to herein as a single separation and concentration device ("S/C device"). One such device is described in U.S. patent application Ser. No. 13/434,245, O'Connell, filed Mar. 29, 2012.

Figure 5:
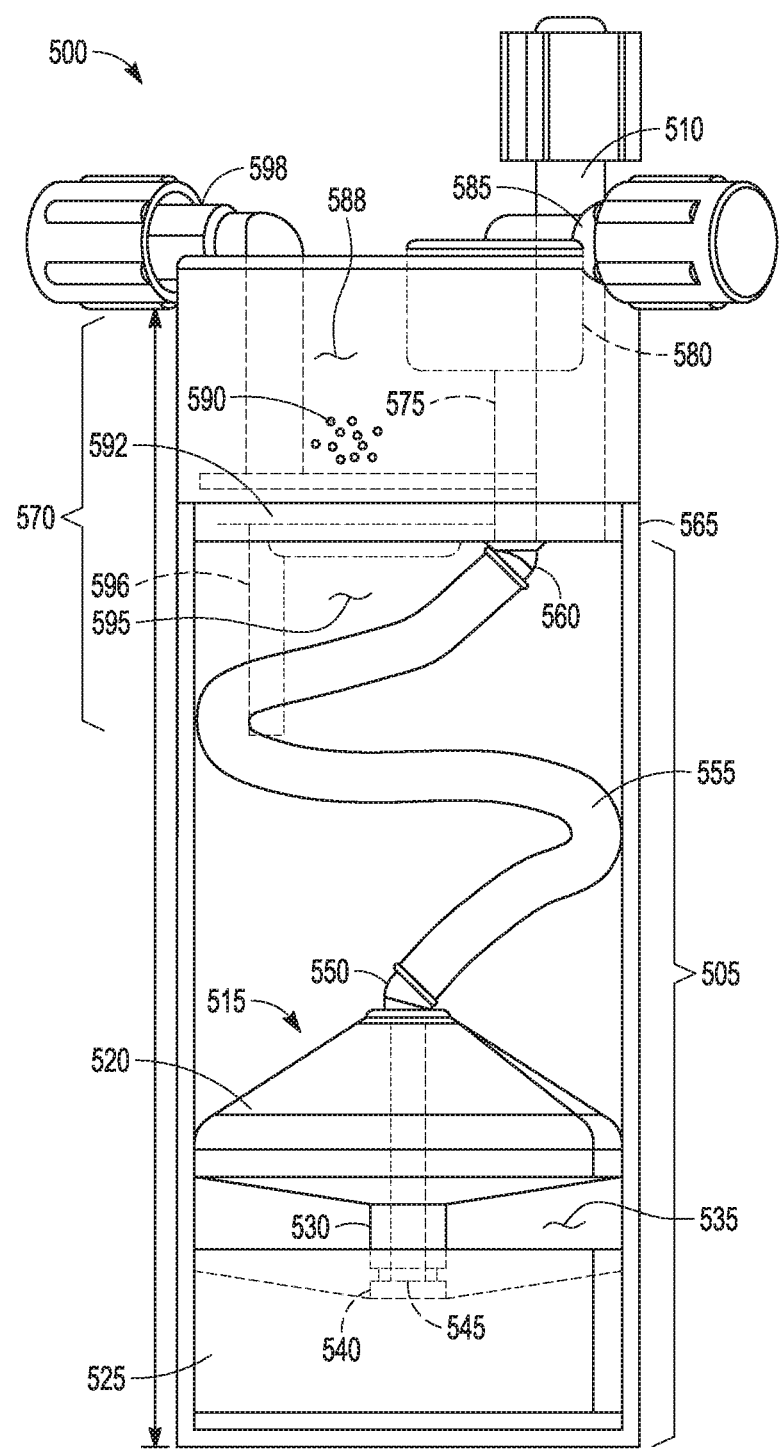
FIG. 5 is a diagram of a single device capable of generating an anti-inflammatory cytokine composition.

The S/C device comprises a separation region, a first concentration region, a second concentration region, a buoy system, an inlet port, a check valve, a first withdrawal port and a second withdrawal port. FIG. 5 shows an S/C device 500 capable of generating an anti-inflammatory cytokine composition from whole blood. For example, the method may start with obtaining a volume of whole blood, which is filled into a separation region 505 of the S/C device 500 by injecting through the inlet port 510. A buoy system 515 is located within the separation region 505. The buoy system comprises a first buoy member 520, a second buoy member 525, and a third buoy member 530 that couples the first buoy member 520 to the second buoy member 525. A space between the first and second buoy members 520, 525 defines a buoy separation region 535. A density of each buoy member can be selected depending on what blood fraction is desired as a result of a separation. The buoy system 515 can include a selected buoy system, such as the buoy system generally used in the GPS® II or GPS®III gravity platelet separation system sold by Biomet Biologics, LLC. (Warsaw, Ind., USA). Buoy systems are disclosed in U.S. Pat. Nos. 7,845,499 and 7,806,276, and 7,992,725.

A method for obtaining a Protein Solution comprises spinning the S/C device 500 by centrifugation. Centrifugal forces allow the buoy system 515 to move through the whole blood, resulting in a fraction of the whole blood to be located in the buoy separation region 535. For example, this fraction may comprise platelet-rich plasma. With a use of a withdrawal syringe, the selected fraction can be removed from the collection volume 535 through the third buoy member 530 that defines a removal passage 540 that is connected with collection face passages 545. A connection elbow 550 can interconnect with the removal passage 540 to allow a vacuum to be formed through the connection elbow 550, the collection passage 540, and the buoy collection passages 545. A collection tube 555 can interconnect the connection elbow 550 with a withdrawal elbow 560 that extends from a wall 565 that can be a bottom wall of concentration region 570. A second withdrawal tube 575 can be first connected with a check valve assembly 580 and a first withdrawal port 585. The first withdrawal port 585 can be connected with the withdrawal syringe with a Luer lock type connection or other appropriate connection.

The check valve assembly 580 ensures the fraction being removed flows in one direction and prevents the fraction being removed from reentering the second withdrawal tube 575. Furthermore, when material is pushed back into the check valve assembly 580 from the first withdrawal port 585, such that material will enter the concentration region 570, a disc within the check valve 580 can flex down towards the second withdrawal tube 575 and close an opening and thereby open a second opening within the check valve assembly 580. The second opening allows the fraction to be pushed into the concentration region 570.

Therefore, the blood fraction is then re-injected through the first withdrawal port 285, through the check valve assembly 580, and into an upper volume 588 of the concentration region 570. Polyacrylamide beads 590 are added to the blood fraction in the upper volume 588 and the blood fraction and the polyacrylamide beads 590 can be mixed by shaking. Optionally, the blood fraction and the beads 590 can be incubated for a selected period of time before proceeding with the method.

The method comprises a second step of spinning by centrifugation. During the second centrifugation, the anti-inflammatory cytokine composition is separated from the beads 590 by being forced through a filter 592 and into a lower concentration region 595 of the concentration region 570. The Protein Solution can be withdrawn through a third withdrawal tube 596 and out a second withdrawal port 598 by use of a second withdrawal syringe. Again, the syringe can be connected to the second withdrawal port by a Luer® lock type connection.

Referring again to FIG. 1, following contacting the liquid with the solid extraction materials, a Protein Solution is isolated, as indicated at step 150. Isolation may be accomplished by drawing off at least a portion of the liquid volume and leaving the beads. In some cases, the extraction material may be sedimented by centrifugation prior to drawing off the Protein Solution. Isolation may also be performed by filtration, where the material is retained by a filter and the Protein Solution passes through the filter using centrifugal force or by using vacuum, for example. If the incubation with extraction material utilizes dry polyacrylamide beads, the liquid volume may be reduced as the beads swell upon rehydration, thereby concentrating the resulting Protein Solution. To maintain the increased concentration, care should be taken in the isolation step so as to avoid compressing the beads or drawing liquid out from the swollen beads. For example, high centrifugal force or high vacuum may collapse the beads and/or draw liquid out of the internal volume of the beads.

Optional Electromagnetic Stimulation

The cytokine cell suspension can be stimulated with an electromagnetic field, before or during the contacting of the liquid with a solid extraction material. Thus, in some embodiments, stimulation of the liquid comprising the cells can be performed prior to contacting the liquid and the solid extraction material. However, it is preferred that at least a portion of the contacting step and at least a portion of the stimulating step overlap in time such that the liquid comprising the cells is concurrently in contact with the solid extraction material and stimulated with the electromagnetic field.

Stimulating the cytokine cell suspension with an electromagnetic field may involve various forms of electromagnetic stimulation, such as a pulsed electromagnetic field or a capacitively coupled electromagnetic field. In some embodiments, the liquid is stimulated using a power source coupled to a stimulation coil. The current passing through the coil produces a pulsing magnetic field which induces in the liquid a pulsing electric field. The coil may partially surround the liquid as it is held within a container, such as a tube or syringe. The coil may be integrated into to the container holding the cytokine cell suspension or may be removable. For example, a plastic tube can be formed with an integrated coil or the coil can be temporarily coupled to the container or placed within the container, for example, the tube can be configured so that the coil can be snapped onto the container. The power source can be coupled to the coil as needed to perform the stimulating step.

Stimulation of the liquid with an electromagnetic field may also include placing at least two electrodes across the liquid. Electrical energy may then be applied to the electrodes so as to capacitively couple the electrodes and generate the electromagnetic field there between. The electromagnetic field is therefore able to pass through the liquid so as to increase the rate and/or amount of cytokine production. In other embodiments, electrodes can be used to produce a direct current or one or more coils can be used to produce a pulsed electromagnetic field.

The strength of the electromagnetic field during stimulation can be at least about 0.5 microvolts per centimeter, whether produced by direct current, capacitively coupled current, or pulsed electromagnetic field. In the case of a direct current electrode, the amplitude of the current can be from about 1 to about 200 microamperes, and in some embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied during the stimulating step may be constant or vary over time. For example, a sinusoidal time varying electromagnetic field can be applied using the electrodes placed across the liquid. Such a sinusoidal time varying electromagnetic field can have a peak voltage across the electrodes from about 1 volt to about 10 volts, and in some embodiments, the peak voltage can be about 5 volts. The corresponding electric field produced can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200,000 Hz, and in some embodiments the frequency may be about 60,000 Hz.

The electromagnetic field applied to the liquid may also be a pulsed electromagnetic field. The pulsed electromagnetic field can be induced using an external coil and a pulse generator. In this regard, a pulsed electromagnetic field may have a pulse duration of from about 10 microseconds per pulse to about 2000 microseconds per pulse. The pulse duration in one embodiment can be about 225 microseconds. The pulses may include electromagnetic bursts, in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Furthermore, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L.P., Parsippany, N.J.) or a DC stimulation device such as an SpF® XL IIb spinal fusion stimulator (EBI, L.P., Parsippany, N.J.). Pulsed electromagnetic fields can be produced using various known methods and apparatuses, such as using a single coil or a pair of Helmholtz coils. For example, a suitable apparatus includes the EBI Bone Healing System® Model 2001 (EBI, L.P., Parsippany, N.J.) and the BTBS stimulation coil. With respect to direct current, an electric field may be generated using any known device for generating a direct current electric field, such as for example, the Osteogen™ implantable bone growth stimulator (EBI, L.P., Parsippany, N.J.). Other suitable devices for generating electromagnetic fields may be used.

Electromagnetic stimulation of the cytokine cell suspension can be continued and/or repeated as desired with respect to contacting the liquid and the solid extraction material. It should be understood, however, that the step of stimulating the liquid with an electromagnetic field includes fields other than, or in addition to, electric or electromagnetic fields associated with ambient conditions (such the electromagnetic fields generated by casual exposure to radios, telephones, desktop computers or similar devices).

In some embodiments, both the contacting and stimulating steps as shown in FIG. 1 are performed in less than about 1 hour. The contacting and stimulating steps can also be performed at temperatures ranging from about 20° C. to about 37° C. In a preferred embodiment, the temperature of the cytokine cell suspension is kept at about 37° C. during the contacting and stimulating steps. One or both of the contacting and stimulating steps are typically performed ex vivo.

Other Methods for Forming Protein Solutions

The present technology provides other methods for forming Protein Solutions, such as the admixture of proteins and other components and the isolation and concentration of proteins and components without using solid extraction materials. Protein Solutions of the present technology can be made entirely comprising proteins made by such methods, or by addition of proteins made by such methods with components or solutions made by tissue isolation and processing with solid extraction materials, as described above.

For example, various methods provide acellular or substantially acellular Protein Solutions, comprising one or more proteins as described above. Without limiting the scope, mechanism or function of the present technology, such acellular anti-inflammatory cytokine compositions may offer advantages in certain applications, insofar as they may not create an immunogenic response in subjects to whom they are administered.

In particular, by way of example, a Protein Solution may comprise interleukin-1 receptor antagonist (IL-1ra) that is synthetic or recombinant, or isolated from autologous, allogeneic or xenogeneic blood or other biologic sources, aside from the methods described above. For example, Kineret™ (anakinra) is a recombinant, non-glycosylated form of IL-1ra, sold by Amgen Manufacturing, Ltd. (Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005. In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004. When an allogeneic anti-inflammatory cytokine composition is to be generated, multiple sources of IL-1ra from multiple subjects may be pooled together.

More generally, methods for making acellular Protein Solutions can comprise culturing cells in a cell culture that either naturally produce anti-inflammatory cytokines, such as IL-1ra, or cells that are engineered to produce such cytokines. Non-limiting examples of cells that naturally produce anti-inflammatory cytokines include adipose tissue cells, adipocytes, adipose-derived stem cells, stromal cells, bone marrow cells, mesenchymal stem cells, and blood cells.

In various embodiments, cell lines can be engineered to overproduce an anti-inflammatory cytokine. Non-limiting examples of anti-inflammatory cytokines include VEGF, TNF-α, IL-1ra, sTNF-RI, sTNF-RII, PGDF-AB, PDGF-BB, IGF-I, EGF, TGF-β1, sIL-1RII, and HGF. Stable eukaryotic cell lines can be generated that overexpress an anti-inflammatory cytokine by transfecting eukaryotic cells, such as mammalian cells, with recombinant DNA comprising a gene encoding an anti-inflammatory cytokine and a selectable marker. Alternatively, prokaryotes and yeast can be engineered to overexpress an anti-inflammatory cytokine by transformation with recombinant DNA comprising a gene encoding an anti-inflammatory cytokine and a selectable marker. Transformations and transfections can be performed with recombinant DNA molecules comprising a DNA sequencing encoding an anti-inflammatory cytokine, such as IL-1ra, and a selectable marker. Eukaryotic and prokaryotic cells can be engineered to overexpress the anti-inflammatory cytokine constitutively or by induction. Methods for expressing anti-inflammatory cytokines, such as IL-1ra, sTNF-RI, and sTNF-RII, and sIL-RII in eukaryotic and prokaryotic cells are described in U.S. Pat. No. 6,337,072. Ford et al., issued Jan. 8, 2002; and U.S. Application Publication No. 2001/0053764, Sims et al., published Dec. 20, 2001.

When a IL-1ra gene is transcribed in humans, the mRNA can be spliced into four variants, resulting in four isoforms of translated IL-1ra. SEQ ID NOs: 1, 3, 5, and 7 are the cDNAs for IL-1ra isoforms 1-4 respectively, and SEQ ID NOs: 2, 4, 6, and 8 are the amino acid sequences of IL-1ra isoforms 1-4 respectively. Collectively, the IL-1ra isoforms are referred to as "IL-1ra." SEQ ID NO: 9 is the cDNA sequence for sTNF-RI and SEQ ID NO: 10 is the amino acid sequence for sTNF-RI. SEQ ID NO:11 is the cDNA sequence for sTNF-RII and SEQ ID NO:12 is the amino acid sequence for sTNF-RII. SEQ ID NO: 13 is the cDNA sequence for sIL-1RI and SEQ ID NO:14 is the amino acid sequence for sIL-RI. SEQ ID NOs 15 and 17 are the cDNAs for sIL-RIIv1 and sIL-1RIIv3 respectively, and SEQ ID NOs:16 and 18 are the amino acid sequences for sIL-1RIIv1 and sIL-RIIv3 respectively. The cDNA sequence for IL-1RIIv2 is a non-coding sequence; therefore, it is not included.

To express either IL-1ra, sTNF-RI, or sTNF-RII (generically referred to as a "protein of interest") in a prokaryotic culture, for example in a particular bacteria, a cDNA sequence (SEQ ID NOs: 1, 3, 5, 7, 9, 11, 13, 15, or 17) is cloned into an expression vector suitable for the bacteria. The expression vector should comprise a strong promoter, and a selectable marker, such as antibiotic resistance. Non-limiting examples of antibiotics capable of killing bacteria cells include ampicillin, tetracycline, kanamycin, and chloramphenicol. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. For example, an N or C-terminal His tag can be used to detect proteins with anti-His antibodies, and they allow for purification on nickel columns. When the expression vector comprising a gene expressing a protein of interest is prepared, a bacteria cell, for example E. coli, can be transformed with the expression vector. The selectable marker ensures that only cells transformed with the vector will survive in LB broth supplemented with an antibiotic corresponding to the selectable marker. The bacteria can then be grown in LB broth supplemented with the antibiotic for expression and purification. Expression vectors, methods for cloning a protein of interest into an expression vector, methods for transforming prokaryotic cells, methods for expressing protein from transformed prokaryotic cells, and protein purification methods are commonly known by those with ordinary skill in the art.

To express a protein of interest in a eukaryotic culture, for example in mammalian cells, a cDNA sequence (SEQ ID NOs: 1, 3, 5, 7, 9, 11, 13, 15, or 17) is cloned into an expression vector suitable for a particular mammalian cell. The expression vector should comprise a strong promoter, and a selectable marker, such as antibiotic resistance. Non-limiting examples of antibiotics capable of killing mammalian cells include geneticin and gentamicin. The expression vector should further comprise elements that result in constitutive or inducible expression of the protein of interest. Optionally, a DNA sequence corresponding to a tag functionally coupled to the protein of interest that allows for identification and purification of the protein can be present in the vector adjacent to the gene for the protein of interest. When the expression vector comprising a gene expressing a protein of interest is prepared, a mammalian cell, such as a human cell, can be transfected with the expression vector. Transfected cells can be grown in a cell culture medium supplemented with an antibiotic corresponding to the selectable marker. The presence of the antibiotic allows for the isolation of stable cell lines. Stable cell lines can then be grown in cell culture medium supplemented with antibiotic for expression and purification. Expression vectors, methods for cloning a protein of interest into an expression vector, methods for transfecting eukaryotic cells and developing stable cell lines, methods for expressing protein from transfected eukaryotic cells, and protein purification methods are commonly known by those with ordinary skill in the art.

Alternatively, eukaryotic cells that have not been genetically altered by DNA transfection can be cultured. The eukaryotic cells can be primary cultures, i.e. cells grown directly from a eukaryotic donor, such as a human, or the eukaryotic cells can be established cell lines. Many established cell lines are available commercially from American Type Culture Collection, Inc. (Manassas, Va., USA). The cells can be grown with or an exogenous signal, such as a recombinant protein. Eukaryotic cells are often cultured in culture flasks with cell culture medium. The cell culture medium can be recovered from the flasks, and centrifuged to remove any non-adherent cells.

A cell culture can be a monolayer culture, a non-adherent culture, or a bioreactor. A monolayer culture comprises anchorage-dependent cells that are cultured on a suitable substrate that allows cell adhesion and spreading, such as cell culture flasks and cell culture dishes. A non-adherent culture comprises cells that are maintained in a suspension. Suitable cells are either not anchorage-dependent, or they are anchorage-dependent cells that have been adapted for culture in a suspension. Many cell lines, for example many insect cells, can be grown in either a monolayer or a suspension. A bioreactor is a device that can support a biologically active environment in which chemical processes are carried out and/or biochemically active substances are derived. Bioreactors can include suspended or immobilized cells. Monolayer cultures, non-adherent cultures, and bioreactors can be maintained by methods commonly used in the art.

In some embodiments, the cell culture is subjected to an electromagnetic field, so as to stimulate the production of one or more proteins. Stimulating the culture with an electromagnetic field may involve various forms of electromagnetic stimulation, such as a pulsed electromagnetic field or a capacitively coupled electromagnetic field. Methods and conditions for stimulation include those discussed above.

Cell cultures can either release anti-inflammatory cytokines into culture medium naturally, or the cultures can be induced to release the anti-inflammatory cytokines into the culture medium. The culture medium can be isolated by aspiration, centrifugation or filtration to form the acellular anti-inflammatory cytokine composition.

In some embodiments, an anti-inflammatory cytokine is isolated from urine, for use in producing a Protein Solution of the present technology. Proteins can be isolated from urine by methods among those known in the art. One such method is employed in the ProteoSpin™ Urine Protein Concentration Maxi Kit sold by Norgen Biotek Corp. (Thorold, Ontario, Canada). This kit utilizes an ion exchange resin integrated into a spin column. Briefly, a urine sample is obtained and its pH adjusted to 3.5. The urine is then transferred to a spin column containing the ion exchange resin, which is placed in a collection tube. The column is then centrifuged, wherein the proteins attach to the resin, and the remaining fluids and salts flow into the collection tube and are discarded. The proteins are then washed by applying supplied column activation and wash buffer followed by centrifugation. The flow through is discarded and the wash procedure is repeated. An elution buffer (10 mM sodium phosphate, pH 12.5) is added to the column and neutralizer is added to an elution tube. The spin column containing the elution buffer is placed in the elution tube and centrifuged, whereby the proteins are eluted and captured in the elution tube containing neutralizer.

Platelet-Poor Plasma

The present technology provides methods for inducing M1 polarization of macrophages in humans or other mammalian subjects using platelet-poor plasma. Platelet-poor plasma (PPP) can be isolated by any means commonly used in the art. For example, PPP can be isolated by a variety of methods, including by density fractionation of blood, cryo-precipitation, and filtration. Density fractionation includes single stage centrifugation, centrifugation in multiple stages, and continuous flow centrifugation.

As described above, FIG. 2 shows a device suitable for fractionating whole blood into various fractions, including PPP. The device 200 includes a container 215, such as a tube, that is placed in a centrifuge after being filled with blood. The container 215 includes a buoy system having an isolator 255 and a buoy 221. The buoy 221 has a selected density which is tuned to reach a selected equilibrium position upon centrifugation; this position lies between a more dense blood fraction and a less dense blood fraction. During centrifugation, the buoy 221 separates the blood within the container 215 into at least two fractions, without substantially commingling the fractions, by sedimenting to a position between the two fractions. In this regard, the isolator 255 and the buoy 221 define a layer comprising platelet-rich plasma 225, while less dense platelet-poor plasma 230 generally fractionates above the isolator 255, and more dense red blood cells 278 generally fractionate below the buoy 221. Following centrifugation, a syringe or tube may then be interconnected with a portion of the buoy system to extract one or more selected fractions for use as the blood component. Therefore PPP 230 can be isolated form the device 200 after centrifugation. Devices including those disclosed in FIG. 2 and associated methods are described in U.S. Patent Application Publication 2004/0251217, Leach et al., published Dec. 12, 2004; and U.S. Patent Application Publication 2005/0109716, Leach et al., published May 26, 2005; both of which are incorporated by reference herein. One such device that is commercially available is the GPS® Platelet Concentrate System, from Biomet Biologics, Inc. (Warsaw, Ind.).

In various embodiments, PPP is concentrated in order to form concentrated PPP. Devices suitable for preparing concentrated PPP are shown in FIGS. 3A and 3B. During use, a fluid containing PPP is injected to the upper chamber via the inlet port and mixed with the polyacrylamide beads. The PPP and polyacrylamide beads may be mixed by rotating the agitator stem and the gel bead agitator, to help mix the PPP and beads. The mixed PPP and polyacrylamide beads are then incubated for the desired time at the desired temperature. The device is then centrifuged so that liquid passes to the lower chamber while the polyacrylamide beads are retained by a filter, thereby separating the polyacrylamide beads from the resulting solution of concentrated PPP that collects in the lower chamber. The solution may be removed from the device via an outlet port. The Plasmax™ Plus Plasma Concentrator, commercially available from Biomet Biologics, LLC (Warsaw, Ind., USA), is an exemplary device suitable for concentrating PPP.

Therapeutic Compositions

The present technology also provides compositions comprising a Protein Solution and a second component comprising active materials, physiological carriers, and combinations thereof. In some embodiments, compositions comprise a safe and effective amount of the Protein Solution and a safe and effective amount of a second active. A "safe and effective" amount of a component is an amount that is sufficient to have the desired therapeutic effect in the human or other mammalian subject, without undue adverse side effects (such as toxicity, irritation, or allergic response), commensurate with a reasonable benefit/risk ratio when used in the manner of this technology. The specific safe and effective amount of the component will, obviously, vary with such factors as the particular condition being treated, the physical condition of the patient, the nature of concurrent therapy (if any), the specific components used, the specific route of administration and dosage form, the carrier (if any) employed, and the desired dosage regimen.

Active materials among those useful herein include biologics and pharmaceutical actives. Biologics include blood fractions, such as PRP, blood products, and concentrated bone marrow aspirate (cBMA).

Accordingly, in some embodiments, the present technology provides compositions comprising a safe and effective amount of a Protein Solution and a safe and effective amount of cBMA. cBMA can include hematopoietic, stem cells, stromal stem cells, mesenchymal stem cells, endothelial progenitor cells, red blood cells, white blood cells, fibroblasts, reticulocytes, adipose cells, or endothelial cells. As described above, the Protein Solution may be made using bone marrow aspirate as a cytokine containing tissue. However, a therapeutic composition may additionally comprise cBMA with Protein Solution. In one embodiment, a therapeutic composition comprises a Protein Solution and cBMA in an Protein Solution:cBMA ratio of about 1:1, about 1:2, about 1:3, about 1:4, about 1:5, about 1:6, about 1:7, about 1:8, about 1:9 or about 1:10. Alternatively, the Protein Solution:cBMA ratio can be about 2:1, about 3:1, about 4:1, about 5:1, about 6:1, about 7:1, about 8:1, about 9:1 or about 10:1. The cBMA and Protein Solution may also be produced simultaneously. Thus, in reference to FIG. 1 and the processes described above, bone marrow aspirate may be added to the whole blood obtained in step 115, prior to or during the contacting with a solid extraction material in step 140; such a process involves operation of both steps 115 and 130. For example, bone marrow aspirate may be added to whole blood prior or during isolation of platelet-rich plasma in step 120. Such methods include those described in U.S. Application Publication No. 2006/0278588, Woodell-May, published Dec. 14, 2006.

In some embodiments, the cBMA and Protein Solution may be may produced simultaneously. Thus, in reference to FIG. 1 and the processes described above, bone marrow aspirate may be added to the whole blood obtained in step 115, prior to or during the contacting with a solid extraction material in step 140; such a process involves operation of both steps 115 and 130. For example, bone marrow aspirate may be added to whole blood prior or during isolation of platelet-rich plasma in step 120. Such methods include those described in U.S. Application Publication No. 2006/0278588, Woodell-May, published Dec. 14, 2006.

Pharmaceutical actives among those useful herein include herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells (other than cytokine-producing cells) such as chondrocytes, bone marrow cells, viruses and virus particles, natural extracts, and combinations thereof. Specific non-limiting examples of bioactive materials include hormones, antibiotics and other anti-infective agents, hematopoietics, thrombopoietics, antiviral agents, antitumor agents (chemotherapeutic agents), antipyretics, analgesics, anti-inflammatory agents, antiallergy agents, vasodilators, cytokines, growth factors, gene regulators, vitamins, minerals and other nutritionals, nutraceuticals and combinations thereof. In some embodiments, compositions may comprise growth factors in addition to those present in the Protein Solution, such Platelet-Derived Growth Factor (PDGF), Transforming Growth Factor Beta (TGF-β), Insulin-Like Growth Factor (IGF), Fibroblast Growth Factor (FGF), Epidermal Growth Factor (EGF). Vascular Endothelial Growth Factor (VEGF), and Bone Morphogenetic Proteins (BMPs).

The compositions may comprise a carrier material, in addition to any liquid comprising the Protein Solution. It should be understood that in various embodiments of the present technology, methods of treatment employ the Protein Solution as comprised and made above, without further carrier, by direct injection or other application to the site of treatment. However, in other embodiments, an additional carrier material may be used for such reasons as for ease of administration, to facilitate administration using a particular delivery device, enhancing activity, and increasing the length of time the Protein Solution remains at the site of administration. Carriers among those useful herein include saline, hyaluronic acid, collagen, buffers (such as Hank's Buffer), cell culture media, blood products (such as PRP and platelet poor plasma), and mixtures thereof.

Protein Solutions, and compositions comprising Protein Solutions may be sterilized prior to administration, by any suitable method. For example, a Protein Solution may be sterilized by including a sterile filter to process the product made by the processes described above. In some embodiments, an antibiotic may be included in the solid extraction material during the contacting step described above, or may be added at one or more of the various steps in the methods and treatments described herein. Alternatively, or in addition, the Protein Solution may be produced aseptically.

Protein Solutions and compositions comprising Protein Solutions may also be lyophilized (freeze drying, or cryodesiccation) after production, using methods among those known in the art. Thus, as depicted in FIG. 1, the Protein Solution can be lyophilized after it is isolated from the solid extraction material. When freeze dried, the anti-inflammatory cytokine composition can be hydrated with a suitable media 170, at a time before administration or at a time of administration. Hydration may be accomplished by mixing the composition with a solution including saline, buffers, blood, blood fractions, bone marrow aspirate, concentrated bone marrow aspirate, and combinations thereof.

The present technology also provides compositions comprising components derived from blood or other tissue that are suitable for allogeneic administration. In particular, such compositions may comprise proteins and other components isolated from a mammalian subject, or a plurality of mammalian subjects, other than the subject to whom the composition is to be administered in a method of this technology. In further reference to FIG. 1, compositions made by contacting a cytokine cell suspension with a solid extraction material may be made suitable for allogeneic administration by freeze drying, as depicted in step 160, after isolation of the Protein Solution from the solid extraction material. In some embodiments, the composition can be processed to remove cytokine-producing cells present in the Protein Solution composition after contacting step 140. Methods for removing cytokine-producing cells include those known in the art, including filtering, clotting, and gravimetric methods. In some embodiments, isolating the blood fraction comprising plasma and removing cytokine-producing cells are performed essentially simultaneously. Thus, the present technology provides methods for making a non-immunogenic anti-inflammatory cytokine composition, comprising:

(a) obtaining a cytokine cell suspension from a mammalian donor;
(b) contacting the liquid with solid extraction material to generate a composition rich in interleukin-1 receptor antagonist;

(c) removing cytokine-producing cells from the composition; and (d) freeze drying the composition to produce the non-immunogenic anti-inflammatory cytokine composition.

In some embodiments, a cryopreservative storage solution is added to the Protein Solution, to provide stability for subsequent storage at reduced temperatures. Suitable storage solutions include those in the art, such as glycerol and dimethylsulfoxide (DMSO). The composition may be stored at reduced temperatures, such as from about 1° C. to about 6° C. In some embodiments, the composition is stored under liquid nitrogen, at about −80° C. Preferably, the cryopreservative storage solution is removed from the Protein Solution prior to administration to a mammalian subject. Removal of the storage solution may be performed by methods including those known in the art for processing stored blood comprising cryopreservative. Washing may be performed using a wash solution, such as saline. In such embodiments, the blood type of the subject to be treated may be matched to the blood type of the donor from whom the cytokine cell suspension was obtained.

Methods of Mediating M2 Macrophage Polarization

The present technology provides methods for inducing M2 polarization of macrophages in a human or other mammalian subject, comprising contacting a Protein Solution of the present technology to a source of macrophages, such as macrophages obtained from the subject. The Protein Solution comprises IL-4, IL-10, IL-1ra, TGFβ, or combinations thereof. Contacting the Protein Solution to monocytes causes polarization of the monocytes into the M2 macrophages.

The present technology provides methods for the treatment of an inflammatory disorder in a human or other mammalian subject, comprising contacting Protein Solution with a source of macrophages to induce the macrophages to polarize into an M2 phenotype, and administering the M2 macrophages to the subject at the site of inflammation, such as to activate Th2 T lymphocytes or to down regulate Th1 T lymphocytes. Inflammatory disorders include rheumatoid arthritis, osteoarthritis, osteolytis, tendonitis, synovitis, peripheral vascular disease, and inflammatory respiratory diseases (such as chronic obstructive pulmonary disease, fibrosis, emphysema, acute respiratory distress syndrome, and pneumonia). Treatment methods also include the prevention, reduction or elimination of pain associated with various disorders, such as pain associated with traumatic injury, muscle strain, arthritis (rheumatoid arthritis and osteoarthritis), synovitis, sacroiliac joint disorders, back disorders, post-surgical injections, tendon injections, sports medicine procedure (for example, ACL repair, MCL repair, BTB repair, patella repair, or cartilage repair), contusions, muscle strains, post traumatic osteoarthritis. Methods also include stimulation of chondrocyte production at the site of a collagen defect, such as defects at joints associated with arthritis, injuries or surgical procedures.

The source of macrophages can be peripheral blood or tissue at or near the site of inflammation. In various embodiments, the steps of contacting Protein Solution with a source of macrophages and administering are performed simultaneously by administering the Protein Solution directly to the peripheral blood or tissue at or near the site of inflammation.

The source of macrophages may also be an isolated source, which comprises an ex-vivo composition comprising macrophages. Such a composition may be a culture of macrophages, a macrophage-containing tissue obtained from a subject (which may be the subject to be treated), or a culture, such as a culture comprising monocytes. Suitable cultures include cultures discussed above regarding cytokine-producing cells.

The source of macrophages may be a concentrated macrophage solution generated by fractionating peripheral blood obtained from the patient. Fractionating peripheral blood comprises preparing a suspension of peripheral blood mononuclear cells (PBMCs) and inducing the PBMCs to differentiate into macrophages. Preparing a suspension of PBMCs from peripheral blood can be performed by any method commonly known in the art. As a non-limiting example, PBMCs can be prepared by Ficoll gradient centrifugation. Ficoll gradient centrifugation includes transferring a volume of Ficoll in a tube, such as a test tube. Whole blood is then gently overlayed onto the Ficoll and the tube is centrifuged for from about 15 minutes to about 60 minutes at from about 175 g to about 225 g at room temperature. In a preferred embodiment, the tube is centrifuged for 45 minutes at 200 g. After centrifugation, there remains a pellet of red blood cells, a Ficoll layer, a white layer comprising PBMCs, and a plasma layer. The white layer comprising PBMCs can then be removed from the tube. Because the PBMCs include monocytes and lymphocytes, the PBMCs can be processed to isolate the monocytes. For example, an Anti-CX3CR1 MicroBeads Kit (Miltenyi Biotec Inc., Auburn, Calif.) can be used to specifically bind monocytes to magnetic beads, which can then be separated from the lymphocytes. Alternatively, the PBMCs can be separated from lymphocytes by flow cytometry techniques, such as fluorescence-activated cell sorting (FACS). After isolation, PBMCs can be cultured in Macrophage Base Medium DXF (PrmoCell), which does not induce differentiation. Differentiation of PBMCs or isolated monocytes into macrophages can be induced by culturing the PBMCs or isolated monocytes, for example, in the presence of differentiation medium containing Protein Solution, macrophage colony-stimulating factor (M-CSF) or granulocyte-macrophage colony-stimulating factor (GM-CSF). In various embodiments, the Protein Solution is the differentiation medium. In other embodiments, the differentiation medium is Macrophage Base Medium DXF (Promocell, Heidelberg, Germany) supplemented with Protein Solution. For example, the differential medium can comprise Macrophage Base Medium DXF supplemented with from about 1% Protein solution to about 75% protein solution. Once differentiated into macrophages, the macrophages can be suspended in a medium or Protein Solution to generate the concentrated macrophage solution. Where the concentrated macrophage solution does not comprise Protein Solution, Protein Solution is contacted with the concentrated macrophage solution to induce M2 polarization of the macrophages. The M2 macrophages can then be administered at or near the site of inflammation.

In some embodiments, the contacting of macrophages with a protein solution comprises mixing the protein solution with an isolated source of macrophages. The resulting mixture may then be administered to the subject, e.g., at the site of an inflammatory disorder.

In various embodiments, methods of the present technology comprise a point-of-care method for making a Protein Solution. As referred to herein, a "point-of-care method" wherein the processes of the present technology are performed at a time proximate to the administration of the Protein Solution to the subject being treated. Such methods may be performed at a location proximate, such as in the same room (for example, bed side) or otherwise immediately adjacent, to the mammalian subject to be treated with the Protein Solution. In various embodiments, a "proximate time" may be, for example, within 12 hours, within 8 hours, within 2 hours, within 1 hour or within 30 minutes of administration of the Protein Solution to the subject.

In some embodiments, the Protein Solution is administered with a concomitant therapy. Such therapies include, for example, the administration of pharmaceutical actives or biologics, as described above. In some embodiments, concomitant therapies are administered concurrently with a Protein Solution. For example, methods may comprise administration of a Protein Solution with a safe and effective amount of an active selected from the group consisting of analgesics and glucocorticosteroids.

In some embodiments, methods comprise administration of a Protein Solution with concentrated bone marrow aspirate, as described above. For example, cBMA and a Protein Solution may be administered concomitantly.

Methods of the present technology may comprise administration of a Protein Solution to the site of inflammation in a mammalian subject to induce M2 polarization of macrophages. Administration of the Protein Solution can be performed with any suitable device, including such devices known in the art for topical delivery of compositions to the muscle and vascular tissue. For example, topical delivery for treatment of inflammation may comprise injection of a Protein Solution in or near a site of inflammation, or at or near tissue adjacent to the site of inflammation.

Methods of Mediating M1 Macrophage Polarization

The present technology provides methods for inducing M1 polarization of macrophages in a human or other mammalian subject, comprising administration of PPP or concentrated PPP to a source of macrophages from the subject. Contacting the PPP or concentrated PPP to monocytes causes polarization of the monocytes into the M1 macrophages.

The present technology further provides methods for the treatment of a disorder associated with cellular proliferation in a human or other mammalian subject, such as by activating Th1 T lymphocytes or to down regulate Th2 T lymphocytes. Such disorders include cancers and bacterial infections. Specific methods include treatment of cancers of the stomach, colon, rectal, liver, pancreatic, lung, breast, cervix uteri, corpus uteri, ovary, prostate (e.g., metastatic prostate cancer), testis, bladder, renal, brain/CNS, head and neck, throat, Hodgkin's disease, non-Hodgkin's lymphoma, multiple myeloma, leukemia, melanoma skin cancer, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma.

Methods comprise contacting PPP or concentrated PPP with a source of macrophages to induce the macrophages to polarize into an M1 phenotype, and administering the M1 macrophages to the subject. The source of macrophages can be peripheral blood or tissue at or near the site of administration. In various embodiments, the steps of contacting PPP or concentrated PPP with a source of macrophages and administering are performed simultaneously by administering the PPP or concentrated PPP directly to the peripheral blood or tissue at or near a site at which M1 macrophages are desired. For example, M1 macrophages can be administered at or near a tumor.

The source of macrophages may also be an isolated source, which comprises an ex-vivo composition comprising macrophages. Such a composition may be a culture of macrophages, a macrophage-containing tissue obtained from a subject (which may be the subject to be treated), or a culture, such as a culture comprising monocytes. Suitable cultures include cultures discussed above regarding cytokine-producing cells. In some embodiments, the contacting of macrophages with PPP comprises mixing the PPP with an isolated source of macrophages. The resulting mixture may then be administered to the subject, e.g., at the site of a cancer or other disorder associated with cellular proliferation.

The source of macrophages may be a concentrated macrophage solution generated by fractionating peripheral blood obtained from the patient. Fractionating peripheral blood comprises preparing a suspension of peripheral blood mononuclear cells (PBMCs) and inducing the PBMCs to differentiate into macrophages. Preparing a suspension of PBMCs from peripheral blood can be performed by any method commonly known in the art. As a non-limiting example, PBMCs can be prepared by Ficoll gradient centrifugation. Ficoll gradient centrifugation includes transferring a volume of Ficoll in a tube, such as a test tube. Whole blood is then gently overlayed onto the Ficoll and the tube is centrifuged for from about 15 minutes to about 60 minutes at from about 175 g to about 225 g at room temperature. In a preferred embodiment, the tube is centrifuged for 45 minutes at 200 g. After centrifugation, there remains a pellet of red blood cells, a Ficoll layer, a white layer comprising PBMCs, and a plasma layer. The white layer comprising PBMCs can then be removed from the tube. Because the PBMCs include monocytes and lymphocytes, the PBMCs can be processed to isolate the monocytes. For example, an Anti-CX3CR1 MicroBeads Kit (Miltenyi Biotec Inc., Auburn, Calif.) can be used to specifically bind monocytes to magnetic beads, which can then be separated from the lymphocytes. Alternatively, the PBMCs can be separated from lymphocytes by flow cytometry techniques, such as fluorescence-activated cell sorting (FACS).

After isolation, PBMCs can be cultured in Macrophage Base Medium DXF (PrmoCell), which does not induce differentiation. Differentiation of PBMCs or isolated monocytes into macrophages can be induced by culturing the PBMCs or isolated monocytes, for example, in the presence of differentiation medium containing PPP, macrophage colony-stimulating factor (M-CSF) or granulocyte-macrophage colony-stimulating factor (GM-CSF). In various embodiments, the Protein Solution is the differentiation medium. In other embodiments, the differentiation medium is Macrophage Base Medium DXF (Promocell, Heidelberg. Germany) supplemented with PPP or concentrated PPP. For example, the differential medium can comprise Macrophage Base Medium DXF supplemented with from about 1% PPP or concentrated PPP to about 75% PPP or concentrated PPP. Once differentiated into M1 macrophages, the M1 macrophages can be suspended in a medium, PPP, or concentrated PPP to generate the concentrated macrophage solution. Where the concentrated M1 macrophage solution does not comprise PPP or concentrated PPP, PPP or concentrated PPP is contacted with the concentrated macrophage solution to induce M1 polarization of the macrophages. The M1 macrophages can then be administered at or near the site of the disorder to be treated, e.g., to a cancerous tissue.

In various embodiments, methods of the present technology comprise a point-of-care method for making PPP or concentrated PPP. As referred to herein, a "point-of-care method" wherein the processes of the present technology are performed at a time proximate to the administration of the PPP to the subject being treated. Such methods may be performed at a location proximate, such as in the same room (for example, bed side) or otherwise immediately adjacent, to the mammalian subject to be treated with the PPP or concentrated PPP. In various embodiments, a "proximate time" may be, for example, within 12 hours, within 8 hours, within 2 hours, within 1 hour or within 30 minutes of administration of the PPP to the subject.

In some embodiments, the PPP or concentrated PPP is administered with a concomitant therapy. Such therapies include, for example, the administration of pharmaceutical actives or biologics, as described above. In some embodiments, concomitant therapies are administered concurrently with PPP or concentrated PPP. For example, methods may comprise administration of PPP or concentrated PPP with a safe and effective amount of an active selected from the group consisting of analgesics and glucocorticosteroids.

In some embodiments, methods comprise administration of PPP or concentrated PPP with concentrated bone marrow aspirate. For example, cBMA and PPP or concentrated PPP may be administered concomitantly.

Methods of the present technology generally comprise administration of PPP or concentrated PPP to a site in a mammalian subject to induce M1 polarization of macrophages. Administration of PPP or concentrated PPP can be performed with any suitable device, including such devices known in the art for topical delivery of compositions to the muscle and vascular tissue. For example, topical delivery for a treatment may comprise injection of PPP or concentrated PPP in or near a site to be treated, or at or near tissue adjacent to the site to be treated.

Array, Aushon Biosystems, Billerica, Mass.). The analytes included IL-4, IL-10, IL-11, IL-13, IL-1ra, IFN-γ, sTNF-RI, sTNF-RII, IL-1α, IL-1β, TNF-α, IL-17, IL-18, bFGF, TBF-β1, and TBF-β2.

The solution contains both anabolic (bFGF, TGF-β1, TGF-β2 (see Table 3)) and anti-inflammatory (IL-1ra, sTNF-RI, sTNF-RII, IL-4, IL-10, IL-11, IL-13, IFN-γ, (see Table 4)) cytokines without expressing large doses of catabolic cytokines (IL-1α, IL-1β, TNF-α, IL-17, IL-18 (see Table 5)). The anti-inflammatory cytokines IL-1ra and sTNF-R are all detected in ng/mL quantities, while all of the catabolic analytes were in pg/mL quantities. However, donor-to-donor variability is detected. Correlations between the catabolic cytokines IL-1 and TNF-a and anti-inflammatory analytes IL-1ra and sTNF-R are compared, but no large correlations detected (Table 6). On average, there is about 13,260 times more IL-1ra than IL-1α and about 7,561 times more than IL-1β.

TABLE 3

Anabolic cytokines in the solution.

| Donor | bFGF | TGF-β1 | TGF-β2 |
|---|---|---|---|
| 1 | 18.5 | 1,458,008 | 153,833 |
| 2 | 10.7 | 1,137,404 | 119,545 |
| 3 | 11.9 | 585,298 | 70,544 |
| 4 | 4.9 | 1,342,442 | 162,707 |
| 5 | 20.0 | 1,579,361 | 204,670 |
| 6 | 7.7 | 1,393,746 | 170,345 |
| 7 | 13.9 | 1,474,155 | 174,502 |
| Average ± SD | 12.5 ± 5.5 | 1,281,488 ± 336,345 | 150,878 ± 43,617 |

TABLE 4

Anti-inflammatory cytokines in the solution.

| Donor | IFN-γ | IL-4 | IL-10 | IL-13 | IL-1ra | TNF-RI | TNF-RII | IL-11 |
|---|---|---|---|---|---|---|---|---|
| 1 | <0.4 | 2.1 | 0.5 | 3.5 | 9,660 | 2,728 | 2,249 | <2.0 |
| 2 | <0.4 | 1.3 | 0.3 | 2.8 | 17,477 | 5,320 | 2,900 | <2.0 |
| 3 | <0.4 | <0.8 | 0.3 | 0.1 | 23,126 | 6,247 | 2,446 | <2.0 |
| 4 | 40.4 | 59.9 | 8.9 | 19.9 | 10,458 | 4,374 | 2,612 | <2.0 |
| 5 | 30.2 | 33.9 | 23.3 | 15.8 | 13,462 | 2,763 | 1,394 | <2.0 |
| 6 | 2.6 | 23.3 | 1.4 | 25.6 | 8,813 | 2,992 | 2,716 | <2.0 |
| 7 | 0.7 | 1.2 | 0.6 | 1.8 | 11,277 | 3,330 | 1,915 | <2.0 |
| Average ± SD | 10.7 ± 17.0 | 17.5 ± 22.9 | 5.0 ± 8.7 | 9.9 ± 10.3 | 13,468 ± 5,154 | 3,936 ± 1,356 | 2,319 ± 520 | <2.0 ± 0 |

Embodiments of the present technology are further illustrated through the following non-limiting examples.

Example 1

Preparing and Characterizing a Protein Solution

A Protein Solution rich in interleukin-I receptor antagonist is prepared from seven consented human providers. Blood (55 mL) is drawn into a 60 cc syringe with 5 mL of anticoagulant citrate dextrose solution A (ACD-A, Citra Labs, Braintree, Mass.). Platelet-rich plasma (PRP) is created using the GPS® III platelet concentration system (800-1 003A, Biomet Biologics, Warsaw, Ind.) according to the instructions for use. The solution is generated by adding 6 mL of PRP to a modified Plasmax device containing 1 gram of polyacrylamide beads (Biomet Biologics, Warsaw, Ind.). The IL-1ra solution is removed from the Plasmax devices and frozen at minus 50° C. for the assay. Cytokine content is assayed on a 16-plex ELISA (Searchlight Protein

TABLE 5

Catabolic cytokines in the solution.

| Donor | IL-17 | TNF-α | IL-1α | IL-1β | IL-18 |
|---|---|---|---|---|---|
| 1 | 3.1 | 16.0 | <0.8 | 1.5 | 239 |
| 2 | 1.2 | <2.3 | 2.5 | 3.3 | 559 |
| 3 | 0.7 | <2.3 | 1.8 | 2.3 | 511 |
| 4 | 28.9 | 195 | 0.8 | 1.3 | 329 |
| 5 | 33.8 | 661 | 0.8 | 2.0 | 450 |
| 6 | 22.0 | 105 | 0.3 | 1.7 | 333 |
| 7 | 6.7 | <2.3 | 1.9 | 1.0 | 787 |
| Average ± SD | 13.8 ± 14.1 | 141 ± 241 | 1.3 ± 0.8 | 1.9 ± 0.8 | 458 ± 183 |

TABLE 6

| Correlation analysis. | | |
| --- | --- | --- |
| Analytes compared | $R^2$ | Ratio |
| IL-1ra and IL-1α | 0.46 | 13,260X |
| IL-1ra and IL-1β | 0.45 | 7,561X |
| TNF-RI and TNF-α | 0.17 | 945X |
| TNF-RII and TNF-α | 0.47 | 477X |

Example 2

Generation of IL-1Ra from Platelet-Rich Plasma

An IL-1ra-rich solution is created as follows. Whole blood (70 mL) anticoagulated (10%) with ACD-A (Braintree, Mass., USA) is drawn from 5 healthy volunteers. A portion (10 mL) is reserved for a whole blood measurement. Platelet-rich plasma (PRP) (6 mL) is produced using the GPS® II System (Biomet Biologics, LLC, Warsaw, Ind., USA). Complete blood counts are collected for the whole blood and PRP samples following a validated procedure, as described in Woodell-May J E, Ridderman D N, Swift M J, Higgins J. "Producing Accurate Platelet Counts for Platelet Rich Plasma: Validation of a Hematology Analyzer and Preparation Techniques for Counting" J. Craniofac. Surg. (2005) September 16(5):749-56.

Following the PRP production, 5 mL of the PRP is added to a modified plasma concentration device (Plasmax™, Biomet Biologics LLC, Warsaw, Ind., USA) and incubated with polyacrylamide desiccating beads in the device for 24 hours at room temperature. Following the contact with polyacrylamide beads the electromagnetic field, the plasma concentration device is centrifuged to separate the serum fraction.

To analyze baseline IL-1ra levels at time zero, the whole blood and PRP samples are activated with 50 μL of thrombin and 10% CaCl2 (1,000 units/mL). A blood clot is formed and incubated for 30 minutes at room temperature. Following incubation, the clot is centrifuged for 5 minutes at 3,000 rpm. Serum is collected from the clots and retained for ELISA analysis. The serum fraction from the plasma concentrator does not require activation by thrombin, and is tested directly. All samples are analyzed for IL-1ra using an ELISA kit (IL-1ra Quantikine™ Kit, R&D Systems, Minneapolis, Minn., USA).

The PRP samples result in about an eight-fold increase in platelets, about five-fold increase in total white blood cells (WBCs), about nine-fold increase in the monocyte fraction of the WBCs, and about a three-fold increase in the PMN fraction of the WBCs. The IL-1ra production in the whole blood and PRP samples is correlated most closely to the WBC concentration. The five-fold increase in the PRP is likely due to the increase in WBCs, and both the whole blood and PRP IL-1ra values can be considered baseline IL-1ra content. This is in contrast to the 195-fold increase in IL-1ra following incubation in the plasma concentrator. This plasma concentration device typically results in a 3-fold increase in plasma protein concentration due to a volume reduction caused by the desiccation process. This 3-fold decrease in volume does not account for the levels of increase seen in the amount of IL-1ra. Therefore, this level of increase indicates stimulation of WBCs to produce IL-1ra during the contact with the solid extraction material (e.g., polyacrylamide beads) and electromagnetic field stimulation.

Correlation analysis demonstrates that IL-1ra production is more closely correlated with the increase in WBCs than the platelet content. The IL-1ra levels do not correlate as closely with the WBC population in the PRP. This is not surprising since the WBC are not activated, and the serum is collected by thrombin activation of the plasma. However, it is possible that the WBC, once activated in the plasma concentration device, participate in the significant production of IL-1ra seen in this example.

Example 3

Production of Protein Solution from PRP

Anticoagulated blood (120 cc) is collected from 5 human donors. Platelet-rich plasma (PRP) is prepared using GPS® III disposables (Biomet Biologics LLC, Warsaw. Ind., USA). PRP is loaded into modified plasma concentration devices (Plasmax™, Biomet Biologics LLC, Warsaw, Ind., USA) and processed. The output is divided into 4 groups: IL-1ra in concentrated plasma with and without thrombin activation (1000 U/mL in 1M CaCl2), or cell-free IL-1ra with and without thrombin activation. IL-1ra is measured using ELISA (R&D Systems) over time.

The PRP contacts polyacrylamide beads in the Plasmax™ device while electromagnetic field stimulation is provided using a capacitively coupled electromagnetic field.

Unclotted PRP produces an average of about 50 ng over 24 hrs. The cell-free samples produce about 34 ng without changing over 24 hrs. Once clotted, the elution of IL-1ra is slowed, with only about 30% being eluted after 10 hours. Release in the cell-free samples is also delayed, but eluted 100% of available IL-1ra after 10 hours.

Example 4

Generation of Protein Solution and Characterization of Cytokine Levels in Healthy Subjects and Osteoarthritis Subjects An Autologous Protein Solution (APS) from healthy patients are prepared as follows for the measurement of growth factors. 72 ml of anticoagulated whole blood are drawn by venipuncture from each of six donors. 3 ml of each donor's anticoagulated whole blood are aliquoted into microcentrifuge tubes and frozen at −50° C. 60 ml of the anticoagulated whole blood is loaded into GPS® III disposable devices (Biomet Biologics LLC, Warsaw, Ind., USA), which is processed according to the manufacturer's instructions to produce PRP. The PRP is removed from the GPS® III devices and added to Plasmax™ devices (Biomet Biologics LLC, Warsaw, Ind. USA), which is processed according to the manufacturer's instructions to produce APS. APS is extracted from each device, aliquoted into microcentrifuge tubes, and frozen at −50° C. Each sample, whole blood and PRP, is subjected to three freeze-thaw cycles. Quantikine Human Immunoassays (R&D Systems, Inc., Minneapolis, Minn.) for VEGF, PDGF-BB, PDGF-AB, EGF, TGF-β1, TGF-β2, and IGF-1 are run in duplicate according to the manufacturer's instructions for each APS and whole blood sample.

APS from healthy patients is prepared as above for the measurement of anti-inflammatory cytokines. Quantikine Human Immunoassays (R&D Systems. Inc., Minneapolis, Minn.) for IL-1ra, IL-1β, IL-8, sTNF-RI, TNF-α, IL-6, sTNF-RII, IL-10, IL-13, and IL-4 are run in duplicate according to the manufacturer's instructions for each APS and whole blood sample. Immunoassays are also performed to detect hepatocyte growth factor (HGF) and soluble IL-1RII.

APS from 105 osteoarthritis patients is prepared as above for the measurement of growth factors anti-inflammatory cytokines. The APS is stored at −50° C. or in dry ice.

Cytokine concentrations are compared between healthy donors and OA patients in baseline blood and APS. IL-1β is concentrated at a higher level in OA patients, but the fold increase is still much lower than that of IL-1ra. Other cytokines and growth factors that are concentrated at least to the level of that observed in healthy donors include sTNF-RI, IGF-I, IL-8, VEGF, and IL-6. The soluble cytokines sTNF-RII and sIL-1RII are concentrated to a level not quite as high but very similar to the healthy concentration level. The results are displayed in Table 7.

TABLE 7

Concentration of growth factors and anti-inflammatory cytokines from APS derived from healthy patients and patients with osteoarthritis (in pg/ml).

| Cytokine | | Baseline | | APS | | Fold Increase |
|---|---|---|---|---|---|---|
| | | Average | StDev | Average | StDev | Average |
| VEGF | Healthy | 276 | 109 | 742 | 494 | 2.7 |
| | OA | 484 | 201 | 1710 | 1025 | 3.8 |
| IL-1β | Healthy | 3.4 | 2 | 3.8 | 0.8 | 1.1 |
| | OA | 3.3 | 1.1 | 8.9 | 7.3 | 2.8 |
| IL-8 | Healthy | 74 | 16 | 315 | 198 | 4.3 |
| | OA | 73.5 | 29.6 | 287.9 | 192.7 | 4.2 |
| IL-6 | Healthy | 3.1 | 0.4 | 3.4 | 0.7 | 1.1 |
| | OA | 1.8 | 1.3 | 3 | 3.5 | 1.6 |
| TNF-α | Healthy | ND | ND | 3.4 | 0.7 | ND |
| | OA | 2.4 | 2 | 4.3 | 3 | 5.3 |
| IL-1ra | Healthy | 8092 | 2536 | 30853 | 16737 | 3.8 |
| | OA | 7576 | 2469 | 41896 | 19669 | 5.9 |
| sTNF-RII | Healthy | 2485 | 338 | 9491 | 1387 | 3.8 |
| | OA | 1491 | 492 | 5060 | 1946 | 3.5 |
| PDGF-AB | Healthy | 13400 | 3400 | 91700 | 24100 | 6.8 |
| | OA | 16799 | 5731 | 37889 | 24922 | 2.5 |
| PDGF-BB | Healthy | 4702 | 1027 | 23810 | 6126 | 5.1 |
| | OA | 5306 | 2422 | 11936 | 8655 | 2.5 |
| IGF-I | Healthy | 114000 | 30000 | 155000 | 34000 | 1.4 |
| | OA | 79072 | 22137 | 118060 | 42827 | 1.5 |
| EGF | Healthy | 240 | 71 | 1227 | 300 | 5.1 |
| | OA | 374 | 199 | 707 | 489 | 2.2 |
| sTNF-RI | Healthy | 629 | 76 | 2408 | 338 | 3.8 |
| | OA | 808 | 275 | 3011 | 964 | 3.9 |
| TGF-βI | Healthy | 25717 | 11131 | 181245 | 56420 | 7.1 |
| | OA | 56594 | 56940 | 153567 | 145973 | 4.2 |
| sIL-1RII | Healthy | 11,786 | ND | 26,000 | ND | 2.2 |
| | OA | ND | ND | ND | ND | ND |
| HGF | Healthy | 782 | ND | 3244 | ND | 4.1 |
| | OA | ND | ND | ND | ND | ND |

Example 5

Generation of a Protein Solution from Adipose Tissue

Adipose stromal cells are prepared as follows. Adipose tissue is minced into small pieces (about 1 cm3) and digested in 2 mg/mL type I collagenase (Worthington Biochemical Corp., Lakewood, N.J.) under intermittent mechanical agitation in a water bath at 37° C. for 180 minutes. Digestion can be neutralized by the addition of medium or a blood-derived solution. The cell suspension is centrifuged (300×g for 7 minutes at 25° C.) followed by removal of the supernatant from the cell pellet. The pellet is then re-suspended in a compatible solution to provide a liquid volume comprising adipose stromal cells.

Alternatively, the pellet is suspended with whole blood obtained from the subject, and added to a GPS™ Platelet Concentrate System, from Biomet Biologics, Inc. (Warsaw, Ind.). Following centrifugation, the platelet-rich plasma layer, which also contains the adipose stromal cells, is extracted from the system.

The adipose stromal cells, optionally including platelet-rich plasma, are then combined with polyacrylamide beads and subjected to a pulsed electromagnetic field by using a pair of Helmholtz coils to stimulate production of IL-1ra. The adipose stromal cells and polyacrylamide beads are separated from the liquid solution to obtain a solution rich in IL-1ra.

Example 6

Generation of Protein Solution from Lipoaspirate

A therapeutic composition of IL-1ra is generated from stromal cells isolated from adipose tissue. Isolation of human stromal cells is performed by obtaining human subcutaneous adipose tissue from lipoaspiration/liposuction procedures and digesting the tissue in collagenase type I solution (Worthington Biochemical Corp., Lakewood, N.J.) under gentle agitation for 1 hour at 37° C. The dissociated cells are filtered with 500 µm and 250 µm Nitex filters. The fraction is centrifuged at 300×g for 5 minutes. The supernatant is discarded and the cell pellet is re-suspended in a compatible liquid solution, such as a blood-derived solution.

Example 7

Induction of M2 Polarization of Macrophages

A Protein Solution comprising IL-4, IL10, IL-1ra, and TGFβ is generated from platelet-rich plasma. Isolation of peripheral blood mononuclear cells (PBMCs) is performed by overlaying whole blood on top of a volume of Ficoll in a test tube. The test tube is centrifuged for 45 minutes at 200 g at room temperature. After centrifugation, the white layer comprising PBMCs is removed. PBMCs include monocytes. The PBMCs are then cultured in the Protein Solution to induce the monocytes to polarize into M2 macrophages. The M2 macrophages can be administered to a site of inflammation in a subject.

Example 8

Inducing M2 Polarization of Macrophages with APS

Osteoarthritis (OA) is a debilitating disease driven by inflammatory cytokines and matrix metalloproteinase secreted by inflammatory macrophages. The goal of this study was to determine if APS, which comprises high concentrations of IL-4. IL-10, IL-1ra, and TGF-β, induces macrophages to assume an M2 regenerative phenotype.

Blood from human donors was processed using an APS device system (Biomet, Warsaw, Ind.) to produce APS and platelet-poor-plasma (PPP). Specifically, PPP and PRP was created using the GPS® III platelet concentration system (800-10 003A. Biomet Biologics, Warsaw, Ind.) according to the instructions for use. APS was then generated by adding the PRP to a modified Plasmax device containing polyacrylamide beads (Biomet Biologics, Warsaw, Ind.). Peripheral blood monocytes were then acquired from the same donors by following Ficoll separation techniques (Stem Cell Technologies, Vancouver, Canada). The monocytes were subsequently cultured using peripheral blood cell macrophage control media (Macrophage Base Medium DXF; Promocell, Heidelberg, Germany) or control media with 10% PPP, 25% PPP, 10% APS, or 25% APS. The cells were cultured for 10 days and then analyzed by epifluorescent microscopy.

APS increased the differentiation of macrophages down the M2 lineage (CD68+ and CD163+) in a dose-dependent manner. Specifically, 35.5±3.8% of macrophages maintained in control media had an M2 phenotype compared to 63.1±12.4% and 65.2±9.8% of macrophages maintained in control media with 10% and 25% APS, respectively. Alternatively, PPP did not have a significant effect on the fraction of M2 macrophages (ANOVA, p>0.05). Also, the APS inhibited the differentiation of macrophages down the M1 pro-inflammatory lineage (CD80+) in a dose dependent manner. For example, 45.9±16.7% of macrophages maintained in control media had an M1 phenotype compared to 43.6±3.2% and 19.4±8.5% of macrophages maintained in control media with 10% and 25% APS, respectively. In contrast. PPP increased the fraction of M1 macrophages in a dose dependent manner.

The results of this study suggest that APS induced the polarization of human macrophages to assume an M2 phenotype. Therefore, inducing macrophages to assume an M2 regenerative phenotype may be a viable treatment for osteoarthritis patients. Additionally, the results show that not all blood fractions polarize monocytes into M2 macrophages. As described above, PPP did not induce an M2 polarization of monocytes. Rather, monocytes cultured in 10% PPP were polarized into inflammatory M1 macrophages.

Example 9

Inducing M1 Polarization of Macrophages with PPP

PPP and PRP was prepared from whole blood with a GPS®III gravity platelet separation system sold by Biomet Biologics, LLC. (Warsaw, Ind., USA). The PRP was further processed in a modified Plasmax device containing polyacrylamide beads (Biomet Biologics, Warsaw, Ind.) to generate APS. Primary blood monocytes were cultured in Macrophage Base Medium DXF (Promocell, Heidelberg, Germany) supplemented with no supplement (control media), 10% PPP, 25%, PPP, 10% APS, or 25% APS for ten days. After the ten days, M1 and M2 macrophages were quantified by probing for CD80 (M1 macrophages) and CD 163 (M2 macrophages).

Figure 6A:
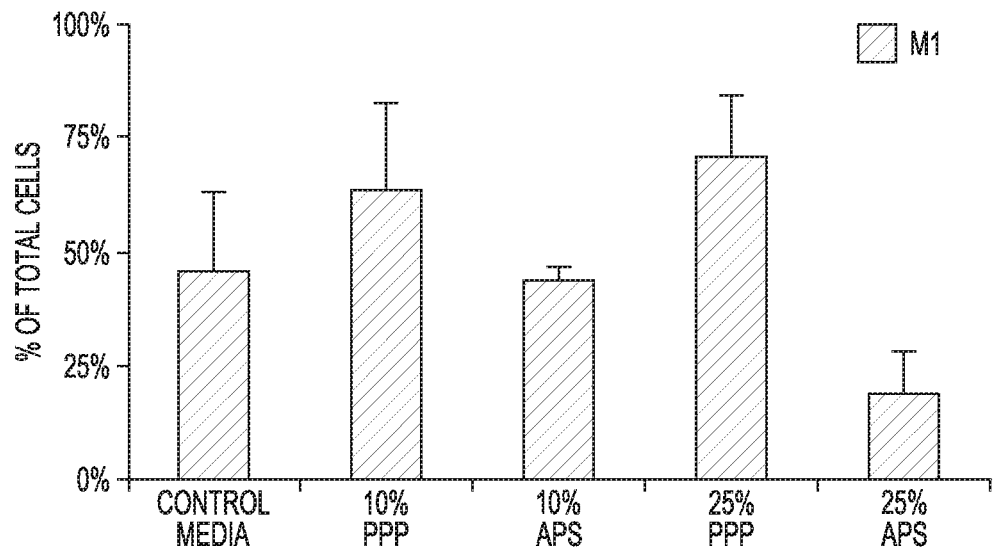
FIG. 6 shows graphs that demonstrate the amount of M1 macrophages (FIG. 6A) and the amount of M2 macrophages (FIG. 6B) present in cultures grown in media supplemented with nothing, platelet-poor plasma (PPP) or autologous protein solution (APS).
Figure 6B:
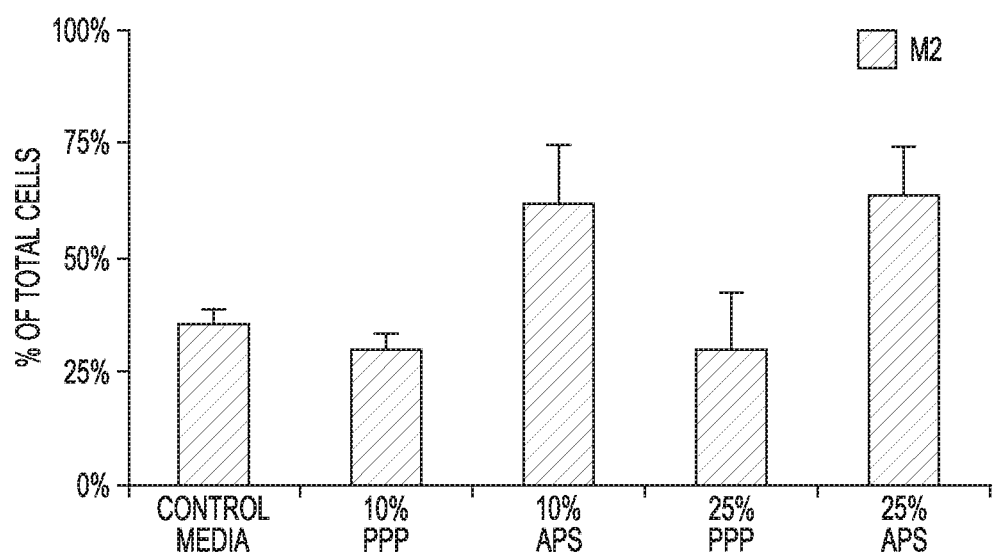

The results of the experiment are shown in FIGS. 6A and 6B. As shown in FIG. 6A, the number of M1 macrophages in the culture with 10% PPP is higher than the number of M1 macrophages in the culture grown in control media. The culture grown in the presence of 25% PPP was higher than that grown in 10% PPP, which indicates that the M1 polarization is dose dependent. The number of M1 macrophages in the cultures grown in 10% APS and 25% APS were equal to the number of M macrophages in the control media, or fewer than the number of M1 macrophages in the control media, respectively.

The opposite results were observed when looking at the amount of M2 macrophages present in the cultures after ten days. As shown in FIG. 6B, the number of M2 macrophages in the cultures grown in 10% PPP and 25% PPP are slightly fewer than the number of M2 macrophages grown in the control media. In contrast, the number of M2 macrophages in the cultures grown in 10% APS and 25% APS are much higher than the number of M2 macrophages present in the control media.

The results obtained through this experiment further demonstrate that monocytes can be polarized into M1 macrophages when grown in the presence of PPP. The results also show that monocytes can be polarized into M2 macrophages when grown in the presence of APS. Accordingly, methods comprise the use of M1 macrophages in the treatment of disorders where it is desirous to have a TH1 cellular immune response. Similarly, methods comprise the use of M2 macrophages in the treatment of disorders where it is desirous to have a TH2 cellular immune response.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all patents and patent applications cited in this disclosure are incorporated by reference herein.

The description and specific examples, while indicating embodiments of the technology, are intended for purposes of illustration only and are not intended to limit the scope of the technology. Equivalent changes, modifications and variations of specific embodiments, materials, compositions and methods may be made within the scope of the present technology, with substantially similar results. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A method for treating inflammation in a subject, comprising:
   administering to the subject at a site of inflammation a composition comprising between about 1 pg/ml and about 60 pg/ml interleukin-4 (IL-4), wherein monocytes or macrophages at the site of inflammation are induced by the composition to polarize to an M2 phenotype.

2. The method according to claim 1, composition comprises monocytes, macrophages, or both, from the subject.

3. The method according to claim 1, wherein the monocytes or macrophages are polarized to an M2 phenotype within 10 days of administering the composition.

4. The method according to claim 1, wherein the composition further comprises interleukin-10 (IL-10), transforming growth factor-beta (TGF-β), vascular endothelial growth factor (VEGF), hepatocyte growth factor (HGF), interleukin-1 receptor antagonist (IL-1ra), or a combination thereof.

5. The method according to claim 1, further comprising obtaining a cytokine cell suspension from a donor; and concentrating the cytokine cell suspension to form the composition.

6. The method according to claim 5, wherein the cytokine cell suspension comprises whole blood, bone marrow aspirate, adipose tissue, a fraction or a concentrate thereof, or a mixture thereof.

7. The method according to claim 5, wherein concentrating includes contacting the cytokine cell suspension with polyacrylamide beads.

8. The method according to claim 1, wherein the composition is prepared from a cytokine cell suspension obtained from the subject.

9. The method according to claim 1, wherein the composition comprises transforming growth factor-beta (TGF-11), vascular endothelial growth factor (VEGF), and hepatocyte growth factor (HGF), each at a concentration greater than the concentration of the respective protein in normal blood.

10. The method according to claim 1, wherein the composition comprises interleukin-10 (IL-10) and transforming growth factor-β(TGF-β), each at a concentration greater than the concentration of the respective protein in normal blood.

11. The method according to claim 1, wherein the composition comprises a protein selected from interleukin-1 receptor antagonist (IL-1ra), soluble tumor necrosis factor-receptor I (sTNF-RI), soluble tumor necrosis factor-receptor II (sTNF-RII), insulin-like growth factor 1 (IGF-I), epidermal growth factor (EGF), hepatocyte growth factor (HGF), platelet-derived growth factor AB (PDGF-AB), platelet-derived growth factor BB (PDGF-BB), vascular endothelial growth factor (VEGF), transforming growth factor-β1 (TGF-β1), soluble interleukin-1 receptor I (sIL-1RI), and soluble interleukin receptor II (sIL-1RII).

12. The method according to claim 1, wherein the composition induces monocytes or macrophages in the composition to polarize to an M2 phenotype.

13. A method for treating inflammation in a subject, comprising:
   obtaining a differentiating composition prepared from a tissue and comprising about 1 pg/ml to about 20 pg/ml interleukin-10 (IL-10); and
   administering the differentiating composition to a site of inflammation in the subject, wherein the differentiating composition induces monocytes or macrophages at the site of inflammation to differentiate to an M2 phenotype.

14. The method according to claim 13, wherein the differentiating composition comprises interleukin-4 (IL-4), transforming growth factor-β (TGF-β), or interleukin-1 receptor antagonist, at a concentration greater than the concentration of the protein in normal blood.

15. The method according to claim 13, wherein the differentiating composition is a concentrated plasma and cytokine cell suspension.

16. The method according to claim 15, wherein the differentiating composition is prepared from whole blood, bone marrow aspirate, adipose tissue, urine, or a fraction, a mixture, or a concentrate of any one or more of the foregoing.

17. A method of treating inflammation in a subject, comprising:
    administering to a site of inflammation in the subject a protein solution prepared from tissue of the subject, the protein solution comprising about 1 pg/ml to about 60 pg/ml interleukin-4 (IL-4) and about 1 pg/ml to about 20 pg/ml interleukin-10 (IL-10) wherein the protein solution induces macrophages or monocytes at the site of inflammation to polarize to an M2 phenotype.

18. The method according to claim 17, wherein the protein solution comprises transforming growth factor-β (TGF-β), vascular endothelial growth factor (VEGF), hepatocyte growth factor (HGF), or a combination thereof.

19. The method according to claim 18, wherein the concentration of TGF-β, VEGF, or HGF in the protein solution is greater than the concentration of the respective protein in normal blood.

20. The method according to claim 17, wherein the protein solution further comprises monocytes isolated from the subject.

* * * * *

UNITED STATES PATENT AND TRADEMARK OFFICE
CERTIFICATE OF CORRECTION

PATENT NO. : 10,946,043 B2
APPLICATION NO. : 15/797796
DATED : March 16, 2021
INVENTOR(S) : Woodell-May et al.

It is certified that error appears in the above-identified patent and that said Letters Patent is hereby corrected as shown below:

On the Title Page

Item (71), in "Applicant", in Column 1, Line 1, delete "Biologies," and insert --Biologics,-- therefor On page 3, in Column 1, under "Other Publications", Line 58, delete "toher acive" and insert --other active-- therefor On page 3, in Column 2, under "Other Publications", Line 17, delete "Inftammation." and insert --Inflammation.-- therefor On page 3, in Column 2, under "Other Publications", Line 25, delete ""Microftuidic" and insert --"Microfluidic-- therefor On page 3, in Column 2, under "Other Publications", Line 31, delete "Coer," and insert --CoCr,-- therefor On page 3, in Column 2, under "Other Publications", Line 35, delete "II-1 Ra" and insert --IL-1Ra-- therefor On page 4, in Column 2, under "Other Publications", Line 1, delete ""Therapuetic" and insert --"Therapeutic-- therefor On page 4, in Column 2, under "Other Publications", Line 5, delete ""Intratrachael" and insert --"Intratracheal-- therefor On page 4, in Column 2, under "Other Publications", Line 28, delete "II-L[Beta] and Tnf[Alpha]-Stimulated" and insert --IL-1β and TNFα-Stimulated-- therefor On page 4, in Column 2, under "Other Publications", Line 40, delete ""IFN-g" and insert --"IFN-gamma-- therefor Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*

In the Claims

In Column 42, Line 5, in Claim 2, after "1,", insert --wherein the--

In Column 42, Line 2, in Claim 9, delete "(TGF-11)," and insert --(TGF-$\beta$),-- therefor